(12) United States Patent
Schalk et al.

(10) Patent No.: US 10,385,361 B2
(45) Date of Patent: Aug. 20, 2019

(54) PRODUCTION OF MANOOL

(71) Applicant: Firmenich SA, Geneva (CH)

(72) Inventors: Michel Schalk, Geneva (CH); Letizia Rocci, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/737,809

(22) PCT Filed: Jun. 30, 2016

(86) PCT No.: PCT/EP2016/065448
§ 371 (c)(1),
(2) Date: Dec. 19, 2017

(87) PCT Pub. No.: WO2017/001641
PCT Pub. Date: Jan. 5, 2017

(65) Prior Publication Data
US 2019/0002925 A1    Jan. 3, 2019

Related U.S. Application Data

(60) Provisional application No. 62/187,236, filed on Jun. 30, 2015.

(30) Foreign Application Priority Data

Jan. 22, 2016 (EP) .................................. 1601249

(51) Int. Cl.
| | |
|---|---|
| *C12P 5/00* | (2006.01) |
| *C12N 15/63* | (2006.01) |
| *C12N 15/74* | (2006.01) |
| *C12N 15/79* | (2006.01) |
| *C12N 9/88* | (2006.01) |
| *C12N 9/90* | (2006.01) |
| *C12N 15/70* | (2006.01) |

(52) U.S. Cl.
CPC ............... *C12P 5/002* (2013.01); *C12N 9/88* (2013.01); *C12N 9/90* (2013.01); *C12N 15/63* (2013.01); *C12N 15/70* (2013.01); *C12N 15/74* (2013.01); *C12N 15/79* (2013.01); *C12P 5/007* (2013.01); *C12Y 402/03* (2013.01); *C12Y 505/01012* (2013.01); *C12Y 505/01014* (2013.01)

(58) Field of Classification Search
CPC ..................... C12Y 505/01012; C12Y 402/03
USPC ........................................................ 435/166
See application file for complete search history.

(56) References Cited

U.S. PATENT DOCUMENTS 4,701,543 A    10/1987    Naef et al.

FOREIGN PATENT DOCUMENTS

| EP | 212254 | 8/1992 |
|---|---|---|
| WO | 2009095366 A1 | 8/2009 |
| WO | 2013064411 A1 | 5/2013 |
| WO | 2014022434 A1 | 2/2014 |

OTHER PUBLICATIONS

International Search Report and Written Opinion for International Application No. PCT/EP2016/065448, dated Aug. 10, 2016.
Caniard, A., et al., "Discovery and functional characterization of two diterpene synthases for sclareol biosynthesis in Salvia sclarea (L.) and their relevance for perfume manufacture," BMC Plant Biology, vol. 12, No. 1, p. 119, 2012.
Ma, Y., et al., "Genome-wide identification and characterization of novel genes involved in terpenoid biosynthesis in Salvia miltiorrhiza," Journal of Experimental Botany, vol. 63, No. 7, p. 2809-2823, 2012.
Cui, G., et al., "Functional divergence of diterpene syntheses in the medicinal plant Salvia miltiorrhiza," Plant Physiology, vol. 169, p. 1607-1618, 2015.
Hasegawa, S., et al. "A diterpene glycoside and lignans from seed of Thujopsis dolabrata," Phytochemistry, vol. 19, No. 11, p. 2479-2481, 1980.
Ohloff, G., "Uberfuhrung des (−)-Sclareols in ( + )-Manool1)" Helvetica Chimica. Acta, vol. 41, p. 845-850, 1958.
Keller, R. K., et al., "Rapid synthesis of isoprenoid diposphates and their isolation in one step using either thin layer or flash chromatography," Journal of Chromatography, vol. 645, No. 1, p. 161-167, 1993.
Tatusova, T. et al., "Blast 2 sequences, a new tool for comparing protein and nucleotide sequences," FEMS Microbiology Letters, vol. 174, p. 247-250, 1999.

*Primary Examiner* — Tekchand Saidha
(74) *Attorney, Agent, or Firm* — Armstrong Teasdale LLP

(57) ABSTRACT

Provided herein are methods of producing (+)-manool comprising: contacting geranylgeranyl diphosphate with an copalyl diphosphate (CPP) synthase to form a (9S, 10S)-copalyl diphosphate wherein the CPP synthase comprises an amino acid sequence having at least 90%, 95%, 98%, 99% and 100% sequence identity to a polypeptide selected from the group consisting of SEQ ID NO: 1 and SEQ ID NO:2; and contacting the CPP with a sclareol synthase enzyme to form (+)-manool.

5 Claims, 4 Drawing Sheets
Specification includes a Sequence Listing.

- Figure 1 -
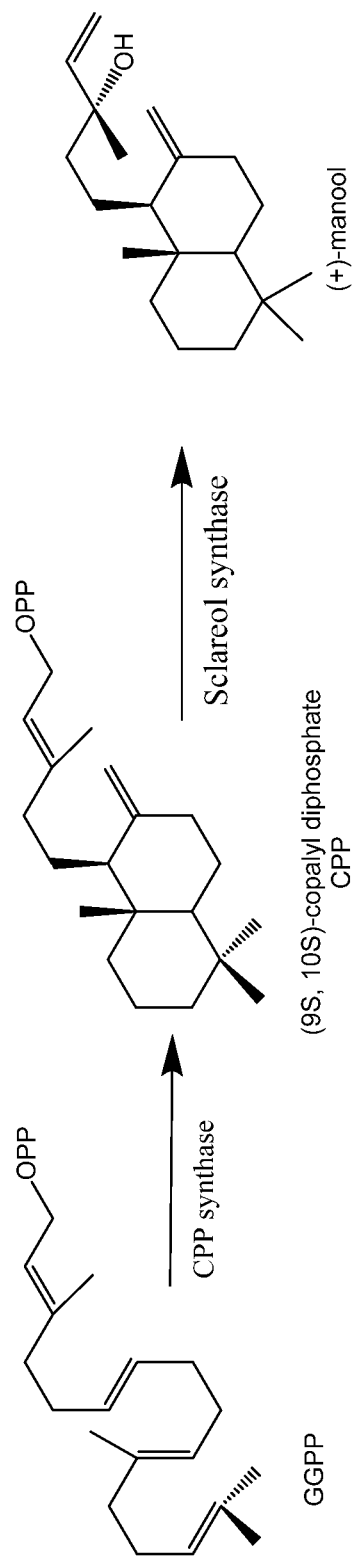

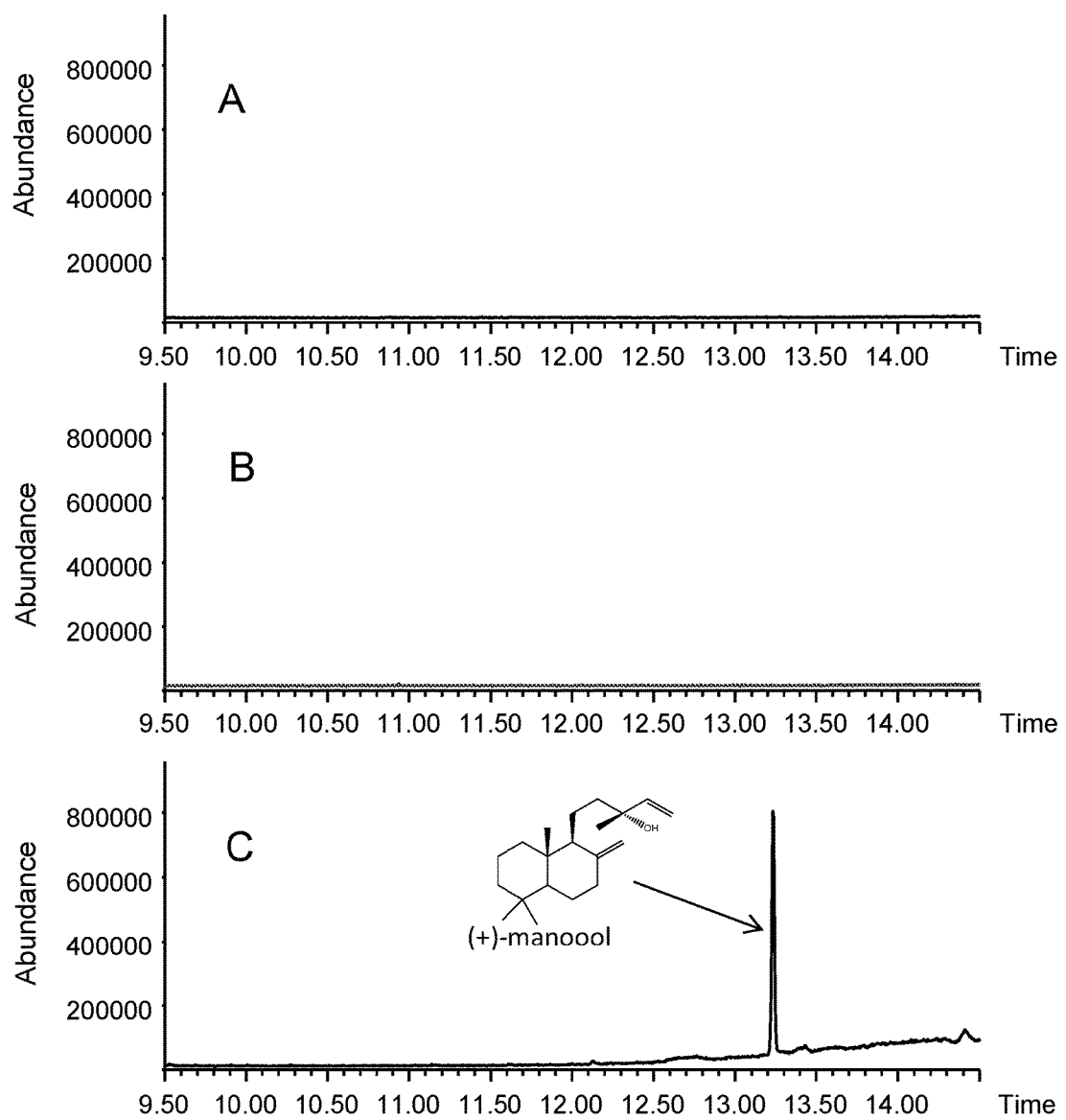
- Figure 2 -

- Figure 3 -
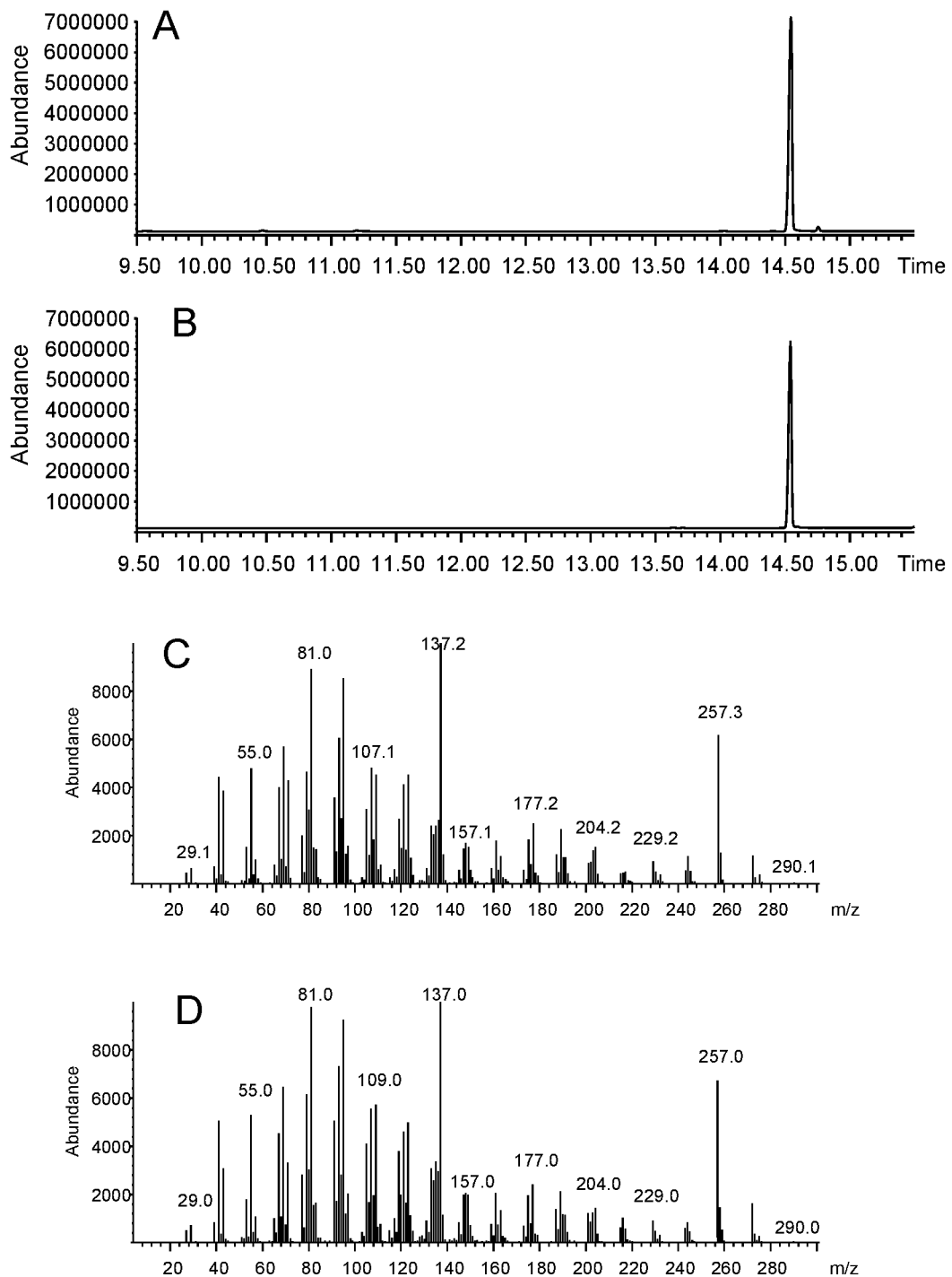

- Figure 4 -
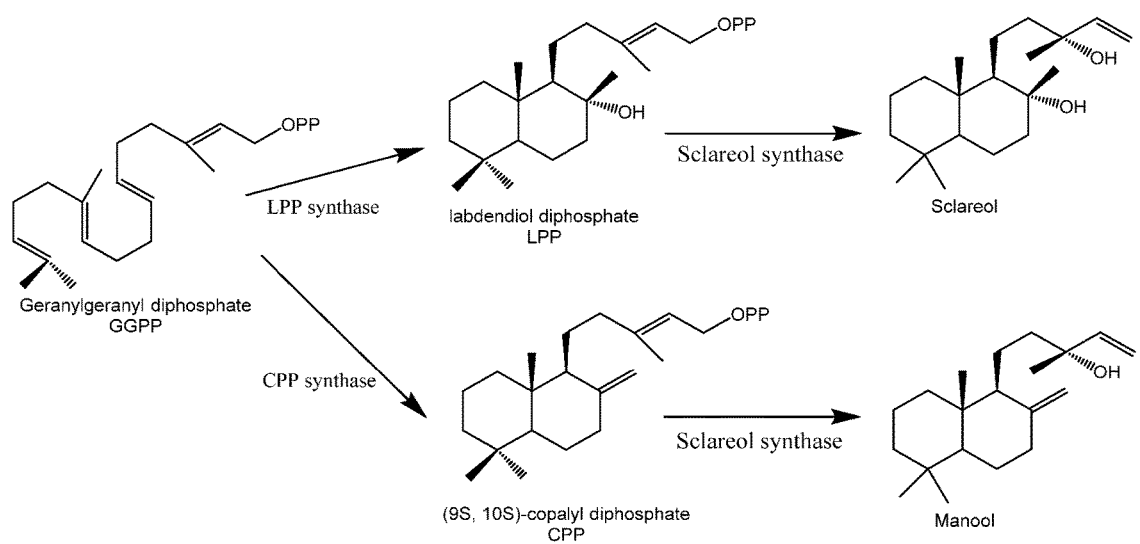

SEQUENCE LISTING

<160> NUMBER OF SEQ ID NOS: 10

<210> SEQ ID NO 1
<211> LENGTH: 793
<212> TYPE: PRT
<213> ORGANISM: Salvia miltiorrhiza

<400> SEQUENCE: 1

```
Met Ala Ser Leu Ser Ser Thr Ile Leu Ser Arg Ser Pro Ala Ala Arg
 1               5                   10                  15

Arg Arg Ile Thr Pro Ala Ser Ala Lys Leu His Arg Pro Glu Cys Phe
            20                  25                  30

Ala Thr Ser Ala Trp Met Gly Ser Ser Lys Asn Leu Ser Leu Ser
        35                  40                  45

Tyr Gln Leu Asn His Lys Lys Ile Ser Val Ala Thr Val Asp Ala Pro
    50                  55                  60

Gln Val His Asp His Asp Gly Thr Thr Val His Gln Gly His Asp Ala
65                  70                  75                  80

Val Lys Asn Ile Glu Asp Pro Ile Glu Tyr Ile Arg Thr Leu Leu Arg
                85                  90                  95

Thr Thr Gly Asp Gly Arg Ile Ser Val Ser Pro Tyr Asp Thr Ala Trp
            100                 105                 110

Val Ala Met Ile Lys Asp Val Glu Gly Arg Asp Gly Pro Gln Phe Pro
        115                 120                 125

Ser Ser Leu Glu Trp Ile Val Gln Asn Gln Leu Glu Asp Gly Ser Trp
    130                 135                 140

Gly Asp Gln Lys Leu Phe Cys Val Tyr Asp Arg Leu Val Asn Thr Ile
145                 150                 155                 160

Ala Cys Val Val Ala Leu Arg Ser Trp Asn Val His Ala His Lys Val
                165                 170                 175

Lys Arg Gly Val Thr Tyr Ile Lys Glu Asn Val Asp Lys Leu Met Glu
            180                 185                 190

Gly Asn Glu Glu His Met Thr Cys Gly Phe Glu Val Val Phe Pro Ala
        195                 200                 205

Leu Leu Gln Lys Ala Lys Ser Leu Gly Ile Glu Asp Leu Pro Tyr Asp
    210                 215                 220

Ser Pro Ala Val Gln Glu Val Tyr His Val Arg Glu Gln Lys Leu Lys
225                 230                 235                 240

Arg Ile Pro Leu Glu Ile Met His Lys Ile Pro Thr Ser Leu Leu Phe
                245                 250                 255

Ser Leu Glu Gly Leu Glu Asn Leu Asp Trp Asp Lys Leu Leu Lys Leu
            260                 265                 270

Gln Ser Ala Asp Gly Ser Phe Leu Thr Ser Pro Ser Ser Thr Ala Phe
        275                 280                 285

Ala Phe Met Gln Thr Lys Asp Glu Lys Cys Tyr Gln Phe Ile Lys Asn
    290                 295                 300

Thr Ile Asp Thr Phe Asn Gly Gly Ala Pro His Thr Tyr Pro Val Asp
305                 310                 315                 320

Val Phe Gly Arg Leu Trp Ala Ile Asp Arg Leu Gln Arg Leu Gly Ile
                325                 330                 335

Ser Arg Phe Phe Glu Pro Glu Ile Ala Asp Cys Leu Ser His Ile His
            340                 345                 350

Lys Phe Trp Thr Asp Lys Gly Val Phe Ser Gly Arg Glu Ser Glu Phe
        355                 360                 365
```

```
Cys Asp Ile Asp Asp Thr Ser Met Gly Met Arg Leu Met Arg Met His
    370                 375                 380

Gly Tyr Asp Val Asp Pro Asn Val Leu Arg Asn Phe Lys Gln Lys Asp
385                 390                 395                 400

Gly Lys Phe Ser Cys Tyr Gly Gly Gln Met Ile Glu Ser Pro Ser Pro
                405                 410                 415

Ile Tyr Asn Leu Tyr Arg Ala Ser Gln Leu Arg Phe Pro Gly Glu Glu
                420                 425                 430

Ile Leu Glu Asp Ala Lys Arg Phe Ala Tyr Asp Phe Leu Lys Glu Lys
            435                 440                 445

Leu Ala Asn Asn Gln Ile Leu Asp Lys Trp Val Ile Ser Lys His Leu
450                 455                 460

Pro Asp Glu Ile Lys Leu Gly Leu Glu Met Pro Trp Leu Ala Thr Leu
465                 470                 475                 480

Pro Arg Val Glu Ala Lys Tyr Tyr Ile Gln Tyr Tyr Ala Gly Ser Gly
                485                 490                 495

Asp Val Trp Ile Gly Lys Thr Leu Tyr Arg Met Pro Glu Ile Ser Asn
            500                 505                 510

Asp Thr Tyr His Asp Leu Ala Lys Thr Asp Phe Lys Arg Cys Gln Ala
            515                 520                 525

Lys His Gln Phe Glu Trp Leu Tyr Met Gln Glu Trp Tyr Glu Ser Cys
530                 535                 540

Gly Ile Glu Glu Phe Gly Ile Ser Arg Lys Asp Leu Leu Leu Ser Tyr
545                 550                 555                 560

Phe Leu Ala Thr Ala Ser Ile Phe Glu Leu Glu Arg Thr Asn Glu Arg
                565                 570                 575

Ile Ala Trp Ala Lys Ser Gln Ile Ile Ala Lys Met Ile Thr Ser Phe
            580                 585                 590

Phe Asn Lys Glu Thr Thr Ser Glu Glu Asp Lys Arg Ala Leu Leu Asn
            595                 600                 605

Glu Leu Gly Asn Ile Asn Gly Leu Asn Asp Thr Asn Gly Ala Gly Arg
610                 615                 620

Glu Gly Gly Ala Gly Ser Ile Ala Leu Ala Thr Leu Thr Gln Phe Leu
625                 630                 635                 640

Glu Gly Phe Asp Arg Tyr Thr Arg His Gln Leu Lys Asn Ala Trp Ser
                645                 650                 655

Val Trp Leu Thr Gln Leu Gln His Gly Glu Ala Asp Ala Glu Leu
            660                 665                 670

Leu Thr Asn Thr Leu Asn Ile Cys Ala Gly His Ile Ala Phe Arg Glu
            675                 680                 685

Glu Ile Leu Ala His Asn Glu Tyr Lys Ala Leu Ser Asn Leu Thr Ser
690                 695                 700

Lys Ile Cys Arg Gln Leu Ser Phe Ile Gln Ser Glu Lys Glu Met Gly
705                 710                 715                 720

Val Glu Gly Glu Ile Ala Ala Lys Ser Ser Ile Lys Asn Lys Glu Leu
                725                 730                 735

Glu Glu Asp Met Gln Met Leu Val Lys Leu Val Leu Glu Lys Tyr Gly
            740                 745                 750

Gly Ile Asp Arg Asn Ile Lys Lys Ala Phe Leu Ala Val Ala Lys Thr
            755                 760                 765

Tyr Tyr Tyr Arg Ala Tyr His Ala Ala Asp Thr Ile Asp Thr His Met
770                 775                 780

Phe Lys Val Leu Phe Glu Pro Val Ala
```

<210> SEQ ID NO 2
<211> LENGTH: 736
<212> TYPE: PRT
<213> ORGANISM: Artificial sequence
<220> FEATURE:
<223> OTHER INFORMATION: Truncated protein

<400> SEQUENCE: 2

```
Met Ala Thr Val Asp Ala Pro Gln Val His Asp His Asp Gly Thr Thr
1               5                   10                  15

Val His Gln Gly His Asp Ala Val Lys Asn Ile Glu Asp Pro Ile Glu
            20                  25                  30

Tyr Ile Arg Thr Leu Leu Arg Thr Thr Gly Asp Gly Arg Ile Ser Val
        35                  40                  45

Ser Pro Tyr Asp Thr Ala Trp Val Ala Met Ile Lys Asp Val Glu Gly
    50                  55                  60

Arg Asp Gly Pro Gln Phe Pro Ser Ser Leu Glu Trp Ile Val Gln Asn
65                  70                  75                  80

Gln Leu Glu Asp Gly Ser Trp Gly Asp Gln Lys Leu Phe Cys Val Tyr
                85                  90                  95

Asp Arg Leu Val Asn Thr Ile Ala Cys Val Val Ala Leu Arg Ser Trp
            100                 105                 110

Asn Val His Ala His Lys Val Lys Arg Gly Val Thr Tyr Ile Lys Glu
        115                 120                 125

Asn Val Asp Lys Leu Met Glu Gly Asn Glu Glu His Met Thr Cys Gly
    130                 135                 140

Phe Glu Val Val Phe Pro Ala Leu Leu Gln Lys Ala Lys Ser Leu Gly
145                 150                 155                 160

Ile Glu Asp Leu Pro Tyr Asp Ser Pro Ala Val Gln Glu Val Tyr His
                165                 170                 175

Val Arg Glu Gln Lys Leu Lys Arg Ile Pro Leu Glu Ile Met His Lys
            180                 185                 190

Ile Pro Thr Ser Leu Leu Phe Ser Leu Glu Gly Leu Glu Asn Leu Asp
        195                 200                 205

Trp Asp Lys Leu Leu Lys Leu Gln Ser Ala Asp Gly Ser Phe Leu Thr
    210                 215                 220

Ser Pro Ser Ser Thr Ala Phe Ala Phe Met Gln Thr Lys Asp Glu Lys
225                 230                 235                 240

Cys Tyr Gln Phe Ile Lys Asn Thr Ile Asp Thr Phe Asn Gly Gly Ala
                245                 250                 255

Pro His Thr Tyr Pro Val Asp Val Phe Gly Arg Leu Trp Ala Ile Asp
            260                 265                 270

Arg Leu Gln Arg Leu Gly Ile Ser Arg Phe Phe Glu Pro Glu Ile Ala
        275                 280                 285

Asp Cys Leu Ser His Ile His Lys Phe Trp Thr Asp Lys Gly Val Phe
    290                 295                 300

Ser Gly Arg Glu Ser Glu Phe Cys Asp Ile Asp Asp Thr Ser Met Gly
305                 310                 315                 320

Met Arg Leu Met Arg Met His Gly Tyr Asp Val Asp Pro Asn Val Leu
                325                 330                 335

Arg Asn Phe Lys Gln Lys Asp Gly Lys Phe Ser Cys Tyr Gly Gly Gln
            340                 345                 350

Met Ile Glu Ser Pro Ser Pro Ile Tyr Asn Leu Tyr Arg Ala Ser Gln
```

```
                355                 360                 365
Leu Arg Phe Pro Gly Glu Glu Ile Leu Glu Asp Ala Lys Arg Phe Ala
    370                 375                 380
Tyr Asp Phe Leu Lys Glu Lys Leu Ala Asn Asn Gln Ile Leu Asp Lys
385                 390                 395                 400
Trp Val Ile Ser Lys His Leu Pro Asp Glu Ile Lys Leu Gly Leu Glu
                405                 410                 415
Met Pro Trp Leu Ala Thr Leu Pro Arg Val Glu Ala Lys Tyr Tyr Ile
            420                 425                 430
Gln Tyr Tyr Ala Gly Ser Gly Asp Val Trp Ile Gly Lys Thr Leu Tyr
            435                 440                 445
Arg Met Pro Glu Ile Ser Asn Asp Thr Tyr His Asp Leu Ala Lys Thr
        450                 455                 460
Asp Phe Lys Arg Cys Gln Ala Lys His Gln Phe Glu Trp Leu Tyr Met
465                 470                 475                 480
Gln Glu Trp Tyr Glu Ser Cys Gly Ile Glu Glu Phe Gly Ile Ser Arg
                485                 490                 495
Lys Asp Leu Leu Leu Ser Tyr Phe Leu Ala Thr Ala Ser Ile Phe Glu
            500                 505                 510
Leu Glu Arg Thr Asn Glu Arg Ile Ala Trp Ala Lys Ser Gln Ile Ile
            515                 520                 525
Ala Lys Met Ile Thr Ser Phe Phe Asn Lys Glu Thr Thr Ser Glu Glu
    530                 535                 540
Asp Lys Arg Ala Leu Leu Asn Glu Leu Gly Asn Ile Asn Gly Leu Asn
545                 550                 555                 560
Asp Thr Asn Gly Ala Gly Arg Glu Gly Gly Ala Gly Ser Ile Ala Leu
                565                 570                 575
Ala Thr Leu Thr Gln Phe Leu Glu Gly Phe Asp Arg Tyr Thr Arg His
            580                 585                 590
Gln Leu Lys Asn Ala Trp Ser Val Trp Leu Thr Gln Leu Gln His Gly
            595                 600                 605
Glu Ala Asp Asp Ala Glu Leu Leu Thr Asn Thr Leu Asn Ile Cys Ala
    610                 615                 620
Gly His Ile Ala Phe Arg Glu Glu Ile Leu Ala His Asn Glu Tyr Lys
625                 630                 635                 640
Ala Leu Ser Asn Leu Thr Ser Lys Ile Cys Arg Gln Leu Ser Phe Ile
                645                 650                 655
Gln Ser Glu Lys Glu Met Gly Val Gly Glu Ile Ala Ala Lys Ser
            660                 665                 670
Ser Ile Lys Asn Lys Glu Leu Glu Glu Asp Met Gln Met Leu Val Lys
        675                 680                 685
Leu Val Leu Glu Lys Tyr Gly Gly Ile Asp Arg Asn Ile Lys Lys Ala
    690                 695                 700
Phe Leu Ala Val Ala Lys Thr Tyr Tyr Arg Ala Tyr His Ala Ala
705                 710                 715                 720
Asp Thr Ile Asp Thr His Met Phe Lys Val Leu Phe Glu Pro Val Ala
                725                 730                 735

<210> SEQ ID NO 3
<211> LENGTH: 2211
<212> TYPE: DNA
<213> ORGANISM: Artificial sequence
<220> FEATURE:
<223> OTHER INFORMATION: Optimised DNA sequence
```

<400> SEQUENCE: 3

```
atggcaactg ttgacgcacc tcaagtccat gatcacgatg gcaccaccgt tcaccagggt      60
cacgacgcgg tgaagaacat cgaggacccg atcgaataca ttcgtaccct gctgcgtacc     120
actggtgatg tcgcatcag cgtcagcccg tatgacacgg cgtgggtggc gatgattaaa      180
gacgtcgagg gtcgcgatgg cccgcaattt ccttctagcc tggagtggat tgtccaaaat     240
cagctggaag atggctcgtg gggtgaccag aagctgtttt gtgtttacga tcgcctggtt     300
aataccatcg catgtgtggt tgcgctgcgt agctggaatg ttcacgctca taaagtcaaa     360
cgtggcgtga cgtatatcaa ggaaaacgtg gataagctga tggaaggcaa cgaagaacac     420
atgacgtgtg gcttcgaggt tgttttttcca gccttgctgc agaaagcaaa gtccctgggt     480
attgaggatc tgccgtacga ctcgccggca gtgcaagaag tctatcacgt ccgcgagcag     540
aagctgaaac gcatcccgct ggagattatg cataagattc cgacctctct gctgttctct     600
ctggaaggtc tggagaacct ggattgggac aaactgctga agctgcagtc cgctgacggt     660
agctttctga ccagcccgag cagcacggcc tttgcgttta tgcagaccaa agatgagaag     720
tgctatcaat tcatcaagaa tactattgat accttcaacg gtggcgcacc gcacacgtac     780
ccagtagacg tttttggtcg cctgtgggcg attgaccgtt tgcagcgtct gggtatcagc     840
cgtttcttcg agccggagat tgcggactgc ttgagccata ttcacaaatt ctggacggac     900
aaaggcgtgt tcagcggtcg tgagagcgag ttctgcgaca tcgacgatac gagcatgggt     960
atgcgtctga tgcgtatgca cggttacgac gtggacccga atgtgttgcg caacttcaag    1020
caaaaagatg gcaagtttag ctgctacggt ggccaaatga ttgagagccc gagcccgatc    1080
tataacttat atcgtgcgag ccaactgcgt ttcccgggtg aagaaattct ggaagatgcg    1140
aagcgttttg cgtatgactt cctgaaggaa aagctcgcaa acaatcaaat cttggataaa    1200
tgggtgatca gcaagcactt gccggatgag attaaactgg gtctggagat gccgtggttg    1260
gccaccctgc cgagagttga ggcgaaatac tatattcagt attacgcggg tagcggtgat    1320
gtttggattg gcaagaccct gtaccgcatg ccggagatca gcaatgatac ctatcatgac    1380
ctggccaaga ccgacttcaa acgctgtcaa gcgaaacatc aatttgaatg gttatacatg    1440
caagagtggt acgaaagctg cggcatcgaa gagttcggta tctcccgtaa agatctgctg    1500
ctgtcttact ttctggcaac ggccagcatt ttcgagctgg agcgtaccaa tgagcgtatt    1560
gcctgggcga atcacaaat cattgctaag atgattacga gctttttcaa taaagaaacc    1620
acgtccgagg aagataaacg tgctctgctg aatgaactgg gcaacatcaa cggtctgaat    1680
gacaccaacg gtgccggtcg tgagggtggc gcaggcagca ttgcactggc cacgctgacc    1740
cagttcctgg aaggtttcga ccgctacacc cgtcaccagc tgaagaacgc gtggtccgtc    1800
tggctgaccc agctgcagca tggtgaggca gacgacgcgg agctgctgac caacacgttg    1860
aatatctgcg ctggccatat cgcgtttcgc gaagagattc tggcgcacaa cgagtacaaa    1920
gccctgagca atctgacctc taaaatctgt cgtcagctta gctttattca gagcgagaaa    1980
gaaatgggcg tggaaggtga gatcgcggca aaatccagca tcaagaacaa agaactggaa    2040
gaagatatgc agatgttggt caagctcgtc ctggagaagt atggtggcat cgaccgtaat    2100
atcaagaaag cgtttctggc cgtggcgaaa acgtattact accgcgcgta ccacgcggca    2160
gataccattg acacccacat gtttaaggtt ttgtttgagc cggttgctta a             2211
```

<210> SEQ ID NO 4
<211> LENGTH: 575

<212> TYPE: PRT
<213> ORGANISM: Salvia sclarea

<400> SEQUENCE: 4

Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile
        35                  40                  45

Asp Phe Met Ala Lys Met Lys Glu Asn Phe Lys Arg Glu Asp Asp Lys
    50                  55                  60

Phe Pro Thr Thr Thr Thr Leu Arg Ser Glu Asp Ile Pro Ser Asn Leu
65                  70                  75                  80

Cys Ile Ile Asp Thr Leu Gln Arg Leu Gly Val Asp Gln Phe Phe Gln
                85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
            260                 265                 270

Leu Gln Gln Leu Gln Arg Trp Tyr Ala Asp Cys Arg Leu Asp Thr Leu
        275                 280                 285

Asn Phe Gly Arg Asp Val Val Ile Ile Ala Asn Tyr Leu Ala Ser Leu
    290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335

Ser Ser Gln Glu Cys Asp Lys Ile Ile Glu Leu Val Lys Glu Trp Lys
            340                 345                 350

Glu Asn Pro Asp Ala Glu Tyr Gly Ser Glu Leu Glu Ile Leu Phe
        355                 360                 365

Met Ala Leu Tyr Asn Thr Val Asn Glu Leu Ala Glu Arg Ala Arg Val
    370                 375                 380

Glu Gln Gly Arg Ser Val Lys Glu Phe Leu Val Lys Leu Trp Val Glu
385                 390                 395                 400

```
Ile Leu Ser Ala Phe Lys Ile Glu Leu Asp Thr Trp Ser Asn Gly Thr
            405                 410                 415

Gln Gln Ser Phe Asp Glu Tyr Ile Ser Ser Trp Leu Ser Asn Gly
            420                 425                 430

Ser Arg Leu Thr Gly Leu Leu Thr Met Gln Phe Val Gly Val Lys Leu
            435                 440                 445

Ser Asp Glu Met Leu Met Ser Glu Glu Cys Thr Asp Leu Ala Arg His
450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
            485                 490                 495

Thr Glu Lys Asp Gly Arg Lys Val Ser Glu Asp Glu Ala Ile Ala Glu
            500                 505                 510

Ile Asn Glu Met Val Glu Tyr His Trp Arg Lys Val Leu Gln Ile Val
            515                 520                 525

Tyr Lys Lys Glu Ser Ile Leu Pro Arg Arg Cys Lys Asp Val Phe Leu
            530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
            565                 570                 575

<210> SEQ ID NO 5
<211> LENGTH: 525
<212> TYPE: PRT
<213> ORGANISM: Artificial sequence
<220> FEATURE:
<223> OTHER INFORMATION: Truncated protein

<400> SEQUENCE: 5

Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
            20                  25                  30

Ile Asp Thr Leu Gln Arg Leu Gly Val Asp Gln Phe Phe Gln Tyr Glu
            35                  40                  45

Ile Asn Thr Ile Leu Asp Asn Thr Phe Arg Leu Trp Gln Glu Lys His
        50                  55                  60

Lys Val Ile Tyr Gly Asn Val Thr Thr His Ala Met Ala Phe Arg Leu
65              70                  75                  80

Leu Arg Val Lys Gly Tyr Glu Val Ser Ser Glu Glu Leu Ala Pro Tyr
            85                  90                  95

Gly Asn Gln Glu Ala Val Ser Gln Gln Thr Asn Asp Leu Pro Met Ile
            100                 105                 110

Ile Glu Leu Tyr Arg Ala Ala Asn Glu Arg Ile Tyr Glu Glu Glu Arg
            115                 120                 125

Ser Leu Glu Lys Ile Leu Ala Trp Thr Thr Ile Phe Leu Asn Lys Gln
            130                 135                 140

Val Gln Asp Asn Ser Ile Pro Asp Lys Lys Leu His Lys Leu Val Glu
145                 150                 155                 160

Phe Tyr Leu Arg Asn Tyr Lys Gly Ile Thr Ile Arg Leu Gly Ala Arg
            165                 170                 175

Arg Asn Leu Glu Leu Tyr Asp Met Thr Tyr Tyr Gln Ala Leu Lys Ser
            180                 185                 190
```

```
Thr Asn Arg Phe Ser Asn Leu Cys Asn Glu Asp Phe Leu Val Phe Ala
        195                 200                 205

Lys Gln Asp Phe Asp Ile His Glu Ala Gln Asn Gln Lys Gly Leu Gln
210                 215                 220

Gln Leu Gln Arg Trp Tyr Ala Asp Cys Arg Leu Asp Thr Leu Asn Phe
225                 230                 235                 240

Gly Arg Asp Val Val Ile Ala Asn Tyr Leu Ala Ser Leu Ile Ile
                245                 250                 255

Gly Asp His Ala Phe Asp Tyr Val Arg Leu Ala Phe Ala Lys Thr Ser
                260                 265                 270

Val Leu Val Thr Ile Met Asp Asp Phe Phe Asp Cys His Gly Ser Ser
                275                 280                 285

Gln Glu Cys Asp Lys Ile Ile Glu Leu Val Lys Glu Trp Lys Glu Asn
                290                 295                 300

Pro Asp Ala Glu Tyr Gly Ser Glu Glu Leu Glu Ile Leu Phe Met Ala
305                 310                 315                 320

Leu Tyr Asn Thr Val Asn Glu Leu Ala Glu Arg Ala Arg Val Glu Gln
                325                 330                 335

Gly Arg Ser Val Lys Glu Phe Leu Val Lys Leu Trp Val Glu Ile Leu
                340                 345                 350

Ser Ala Phe Lys Ile Glu Leu Asp Thr Trp Ser Asn Gly Thr Gln Gln
                355                 360                 365

Ser Phe Asp Glu Tyr Ile Ser Ser Ser Trp Leu Ser Asn Gly Ser Arg
                370                 375                 380

Leu Thr Gly Leu Leu Thr Met Gln Phe Val Gly Val Lys Leu Ser Asp
385                 390                 395                 400

Glu Met Leu Met Ser Glu Glu Cys Thr Asp Leu Ala Arg His Val Cys
                405                 410                 415

Met Val Gly Arg Leu Leu Asn Asp Val Cys Ser Ser Glu Arg Glu Arg
                420                 425                 430

Glu Glu Asn Ile Ala Gly Lys Ser Tyr Ser Ile Leu Leu Ala Thr Glu
                435                 440                 445

Lys Asp Gly Arg Lys Val Ser Glu Asp Glu Ala Ile Ala Glu Ile Asn
450                 455                 460

Glu Met Val Glu Tyr His Trp Arg Lys Val Leu Gln Ile Val Tyr Lys
465                 470                 475                 480

Lys Glu Ser Ile Leu Pro Arg Arg Cys Lys Asp Val Phe Leu Glu Met
                485                 490                 495

Ala Lys Gly Thr Phe Tyr Ala Tyr Gly Ile Asn Asp Glu Leu Thr Ser
                500                 505                 510

Pro Gln Gln Ser Lys Glu Asp Met Lys Ser Phe Val Phe
                515                 520                 525

<210> SEQ ID NO 6
<211> LENGTH: 1583
<212> TYPE: DNA
<213> ORGANISM: Artificial sequence
<220> FEATURE:
<223> OTHER INFORMATION: Optimised DNA sequence

<400> SEQUENCE: 6
atggcgaaaa tgaaggagaa ctttaaacgc gaggacgata aattcccgac gaccacgacc      60
ctgcgcagcg aggatatccc gagcaacctg tgcatcattg ataccctgca gcgcctgggt     120
gtcgatcagt tcttccaata cgaaatcaat accattctgg acaatacttt tcgtctgtgg     180
```

-continued

```
caagagaaac acaaagtgat ctacggcaac gttaccaccc acgcgatggc gttccgtttg    240
ttgcgtgtca agggctacga ggtttccagc gaggaactgg cgccgtacgg taatcaggaa    300
gcagttagcc aacagacgaa tgatctgcct atgatcattg agctgtatcg cgcagcaaat    360
gagcgtatct acgaagagga acgcagcctg aaaagatcc tggcgtggac cacgatcttc    420
ctgaacaaac aagttcaaga caattctatt cctgataaga agctgcataa actggtcgaa    480
ttctatctgc gtaattacaa gggcatcacg atccgtctgg cgcacgccg taacctggag    540
ttgtatgata tgacgtatta ccaggctctg aaaagcacca atcgtttctc caatctgtgt    600
aatgaggatt ttctggtgtt cgccaagcag gattttgaca tccacgaggc gcaaaatcaa    660
aaaggtctgc aacaactgca acgttggtac gctgactgtc gcctggacac cctgaatttc    720
ggtcgcgacg ttgtcattat tgcaaactat ctggccagcc tgatcatcgg tgatcacgca    780
ttcgactacg tccgcctggc cttcgctaag accagcgttc tggtgaccat tatggatgat    840
ttcttcgatt gccacggttc tagccaggaa tgcgacaaaa tcattgagct ggtgaaagag    900
tggaaagaaa accctgatgc ggaatacggt tccgaagagt tggagatcct gtttatggcc    960
ttgtacaaca ccgtgaatga actggccgag cgtgctcgtg tggagcaggg ccgttctgtg   1020
aaggagtttt tggtcaagtt gtgggtggaa atcctgtccg cgttcaagat cgaactggat   1080
acgtggtcga atggtacgca acagagcttc gacgaataca tcagcagcag ctggctgagc   1140
aatggcagcc gtctgaccgg tttgctgacc atgcaatttg tgggtgttaa actgtccgat   1200
gaaatgctga tgagcgaaga atgcaccgac ctggcacgcc atgtgtgtat ggtgggtcgc   1260
ctgctgaacg acgtctgcag cagcgaacgt gagcgcgagg aaaacattgc aggcaagagc   1320
tacagcatct tgttggccac cgagaaagat ggtcgcaaag tgtctgagga cgaagcaatt   1380
gcagagatta atgaaatggt cgagtaccac tggcgtaagg ttttgcagat tgtgtataag   1440
aaagagagca tcttgccgcg tcgctgtaag gatgttttct tggagatggc gaagggcacg   1500
ttctatgcgt acggcattaa cgacgagctg acgagcccgc aacaatcgaa agaggacatg   1560
aagagcttcg tgttctgagg tac                                            1583
```

<210> SEQ ID NO 7
<211> LENGTH: 307
<212> TYPE: PRT
<213> ORGANISM: Pantoea agglomerans

<400> SEQUENCE: 7

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
                20                  25                  30

Thr Asp Ser Gln Asp Ile Val Ser Leu Ala Met Arg Glu Gly Val Met
            35                  40                  45

Ala Pro Gly Lys Arg Ile Arg Pro Leu Leu Met Leu Leu Ala Ala Arg
        50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
                100                 105                 110

Lys Phe Gly Glu Ser Val Ala Ile Leu Ala Ser Val Gly Leu Leu Ser

|     |     |     | 115 |     |     |     | 120 |     |     |     | 125 |     |     |
|-----|-----|-----|-----|-----|-----|-----|-----|-----|-----|-----|-----|-----|-----|

Lys Ala Phe Gly Leu Ile Ala Ala Thr Gly Asp Leu Pro Gly Glu Arg
    130                  135              140

Arg Ala Gln Ala Val Asn Glu Leu Ser Thr Val Gly Val Gln Gly
145                150              155              160

Leu Val Leu Gly Gln Phe Arg Asp Leu Asn Asp Ala Ala Leu Asp Arg
                    165              170              175

Thr Pro Asp Ala Ile Leu Ser Thr Asn His Leu Lys Thr Gly Ile Leu
            180              185              190

Phe Ser Ala Met Leu Gln Ile Val Ala Ile Ala Ser Ala Ser Ser Pro
        195                200              205

Ser Thr Arg Glu Thr Leu His Ala Phe Ala Leu Asp Phe Gly Gln Ala
    210                215              220

Phe Gln Leu Leu Asp Asp Leu Arg Asp Asp His Pro Glu Thr Gly Lys
225                230              235              240

Asp Arg Asn Lys Asp Ala Gly Lys Ser Thr Leu Val Asn Arg Leu Gly
            245              250              255

Ala Asp Ala Ala Arg Gln Lys Leu Arg Glu His Ile Asp Ser Ala Asp
        260                265              270

Lys His Leu Thr Phe Ala Cys Pro Gln Gly Gly Ala Ile Arg Gln Phe
    275                280              285

Met His Leu Trp Phe Gly His His Leu Ala Asp Trp Ser Pro Val Met
290                295              300

Lys Ile Ala
305

<210> SEQ ID NO 8
<211> LENGTH: 924
<212> TYPE: DNA
<213> ORGANISM: Artificial sequence
<220> FEATURE:
<223> OTHER INFORMATION: Optimised DNA sequence

<400> SEQUENCE: 8

| | | | | | |
|---|---|---|---|---|---|
| atggtttctg | gttcgaaagc | aggagtatca | cctcataggg | aaatcgaagt | catgagacag | 60 |
| tccattgatg | accacttagc | aggattgttg | ccagaaacag | attcccagga | tatcgttagc | 120 |
| cttgctatga | gagaaggtgt | tatggcacct | ggtaaacgta | tcagacccttt | gctgatgtta | 180 |
| cttgctgcaa | gagacctgag | atatcagggt | tctatgccta | cactactgga | tctagcttgt | 240 |
| gctgttgaac | tgacacatac | tgcttccttg | atgctggatg | acatgccttg | tatggacaat | 300 |
| gcggaactta | agagggtca | accaacaacc | cacaagaaat | tcggagaatc | tgttgccatt | 360 |
| ttggcttctg | taggtctgtt | gtcgaaagct | tttggcttga | ttgctgcaac | tggtgatctt | 420 |
| ccaggtgaaa | ggagagcaca | agctgtaaac | gagctatcta | ctgcagttgg | tgttcaaggt | 480 |
| ctagtcttag | acagttcag | agatttgaat | gacgcagctt | tggacagaac | tcctgatgct | 540 |
| atcctgtcta | cgaaccatct | gaagactggc | atcttgttct | cagctatgtt | gcaaatcgta | 600 |
| gccattgctt | ctgcttcttc | accatctact | agggaaacgt | tacacgcatt | cgcattggac | 660 |
| tttggtcaag | cctttcaact | gctagacgat | ttgagggatg | atcatccaga | gacaggtaaa | 720 |
| gaccgtaaca | agacgctgg | taaaagcact | ctagtcaaca | gattgggtgc | tgatgcagct | 780 |
| agacagaaac | tgagagagca | cattgactct | gctgacaaac | acctgacatt | tgcatgtcca | 840 |
| caaggaggtg | ctataaggca | gtttatgcac | ctatggtttg | gacaccatct | tgctgattgg | 900 |
| tctccagtga | tgaagatcgc | ctaa | | | | 924 |

```
<210> SEQ ID NO 9
<211> LENGTH: 71
<212> TYPE: DNA
<213> ORGANISM: Artificial sequence
<220> FEATURE:
<223> OTHER INFORMATION: Primer sequence

<400> SEQUENCE: 9
ctgtttgagc cggtcgccta aggtaccaga aggagataaa taatggcgaa aatgaaggag     60
aactttaaac g                                                         71

<210> SEQ ID NO 10
<211> LENGTH: 55
<212> TYPE: DNA
<213> ORGANISM: Artificial sequence
<220> FEATURE:
<223> OTHER INFORMATION: Primer sequence

<400> SEQUENCE: 10
gcagcggttt ctttaccaga ctcgaggtca gaacacgaag ctcttcatgt cctct          55
```

PRODUCTION OF MANOOL

RELATED APPLICATIONS

This application is a national stage application under 35 U.S.C. § 371 filing of International Patent Application PCT/EP2016/065448, filed Jun. 30, 2016, which claims the benefit of U.S. Provisional Application No. 62/187,236, filed Jun. 30, 2015 and EP Application 1601249.4, filed Jan. 22, 2016.

TECHNICAL FIELD

Provided herein are biochemical methods of producing (+)-manool using a copalyl diphosphate synthase and a sclareol synthase.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many terpene (e.g. sesquiterpene) molecules are known for their flavor and fragrance properties and their cosmetic, medicinal and antimicrobial effects. Numerous terpene (e.g. sesquiterpene) hydrocarbons and terpenoids (e.g. sesquiterpenoids) have been identified.

Biosynthetic production of terpenes involves enzymes called terpene synthases. These enzymes convert an acyclic terpene precursor in one or more terpene products. In particular, diterpene synthases produce diterpenes by cyclization of the precursor geranylgeranyl pyrophosphate (GGPP). The cyclization of GGPP often requires two enzyme polypeptides, a type I and a type II diterpene synthase working in combination in two successive enzymatic reactions. The type II diterpene synthases catalyze a cyclization/rearrangement of GGPP initiated by the protonation of the terminal double bond of GGPP leading to a cyclic diterpene diphosphate intermediate. This intermediate is then further converted by a type I diterpene synthase catalyzing an ionization initiated cyclization.

Diterpene synthases are present in the plants and other organisms and use substrates such as geranlygeranyl diphosphate but they have different product profiles. Genes and cDNAs encoding diterpene synthases have been cloned and the corresponding recombinant enzymes characterized.

Copalyl diphosphate synthases and sclareol synthases are enzymes that occur in plants. Hence, it is desirable to discover and use these enzymes and variants in biochemical processes to generate (+)-manool

SUMMARY

Provided herein is a method of producing (+)-manool comprising:
  a) contacting geranylgeranyl diphosphate with a copalyl diphosphate (CPP) synthase to form a (9S,10S)-copalyl diphosphate wherein the CPP synthase comprises an amino acid sequence having at least 90%, 95%, 98%, 99% or 100% sequence identity to a polypeptide selected from the group consisting of SEQ ID NO: 1 and SEQ ID NO:2; and
  b) contacting the (9S,10S)-copalyl diphosphate CPP with a sclareol synthase to form (+)-manool; and
  c) optionally isolating the (+)-manool.

Also provided herein is a polypeptide wherein the polypeptide comprises a sequence of amino acids that has at least 90%, 95%, 98%, 99% or 100% sequence identity to a polypeptide selected from the group consisting of SEQ ID NO: 1 and SEQ ID NO:2.

Also provided herein is a nucleic acid encoding a polypeptide described above.

Also provided herein is a nucleic acid wherein the nucleic acid comprises a nucleotide sequence that has at least 90%, 95%, 98%, 99% or 100% sequence identity to SEQ ID NO 3.

Also provided herein is a method for transforming a host cell or non-human organism with a nucleic acid encoding a polypeptide having a copalyl diphosphate synthase activity and a polypeptide having a sclareol synthase activity wherein the polypeptide having the copalyl diphosphate synthase activity comprises an amino acid sequence that has at least 90%, 95%, 98%, 99% or 100% sequence identity to a polypeptide selected from the group consisting of SEQ ID NO: 1 and SEQ ID NO:2 and wherein the polypeptide having the sclareol synthase activity comprises an amino acid sequence that has at least 90%, 95%, 98%, 99% or 100% sequence identity to a polypeptide selected from the group consisting of SEQ ID NO:4 and SEQ ID NO:5. Also provided herein is a host cell or non-human organism produced by the method.

Also provided herein is an expression vector comprising a nucleic acid encoding a CPP synthase wherein the CPP synthase comprises an amino acid sequence having at least 90%, 95%, 98%, 99% or 100% sequence identity to a polypeptide selected from the group consisting of SEQ ID NO: 1 and SEQ ID NO:2, and a nucleic acid encoding a sclareol synthase.

Also provided herein is a non-human host organism or cell comprising at least one nucleic acid encoding a polypeptide having CPP synthase activity, and at least one nucleic acid encoding a polypeptide having sclareol synthase activity, wherein the polypeptide having CPP synthase activity comprises an amino acid sequence that has at least 90%, 95%, 98%, 99% or 100% sequence identity to a polypeptide selected from the group consisting of SEQ ID NO: 1 and SEQ ID NO:2.

Also provided herein is a method for producing (+)manool comprising cultivating a host organism or cell according to the invention.

DESCRIPTION OF THE DRAWINGS

FIG. 1. Enzymatic pathway from geranylgeranyl-diphosphate (GGPP) to (+)-manool.

FIG. 2. GCMS analysis of the in vitro enzymatic conversion of GGPP. A. Using the recombinant SmCPS enzyme. B. Using the recombinant SsScS enzyme. C. Combining the SmCPS with SsScS enzymes in a single assay.

FIG. 3. GCMS analysis of (+)-manool produced using *E. coli* cells expressing SmCPS, SsScS and mevalonate pathway enzymes. A. Total ion chromatogram of an extract of the *E. coli* culture medium. B. Total ion chromatogram of a (+)-manool standard. C. Mass spectrum of the major peak (retention time of 14.55 min) in chromatogram A. D. Mass spectrum of the (+)-manool authentic standard.

FIG. 4. Enzymatic pathways from geranylgeranyl-diphosphate (GGPP) to (+)-manool and sclareol.

DETAILED DESCRIPTION

Abbreviations Used
bp base pair
kb kilo base
DNA deoxyribonucleic acid
cDNA complementary DNA
CPP copalyl diphosphate
DTT dithiothreitol
FPP farnesyl-diphosphate
GGPP geranlgeranyl diphosphate
GC gaseous chromatograph
IPTG isopropyl-D-thiogalacto-pyranoside
LB lysogeny broth
MS mass spectrometer
MVA mevalonic acid
PCR polymerase chain reaction
RNA ribonucleic acid
mRNA messenger ribonucleic acid
miRNA micro RNA
siRNA small interfering RNA
rRNA ribosomal RNA
tRNA transfer RNA
Definitions The term "polypeptide" means an amino acid sequence of consecutively polymerized amino acid residues, for instance, at least 15 residues, at least 30 residues, at least 50 residues. In some embodiments provided herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "biological function," "function," "biological activity" or "activity" refer to the ability of the CPP synthase and the sclareol synthase activity to catalyze the formation of (+)-manool. The "biological function," "function," "biological activity" or "activity" of CPP synthase may, for example, refer to the ability of the CPP synthase to catalyse the formation of (9S,10S)-copalyl diphosphate from GGPP. The "biological function," "function," "biological activity" or "activity" of sclareol synthase may, for example, refer to the ability of the sclareol synthase to catalyse the formation of (+)manool from (9S,10S)-copalyl diphosphate.

A sclareol synthase may refer to an enzyme, e.g. a naturally occurring enzyme, which has the ability to catalyse formation of sclareol from labdendiol diphosphate (LPP) as shown in FIG. 4. LPP can be produced from GGPP by the action of a labdendiol-diphosphate synthase (LPS) (see FIG. 4). For use in the present invention, such a sclareol synthase, as above, also has ability to catalyse the formation of (+)-manool from (9S,10S)-copalyl diphosphate. It will be understood that, e.g. variant, fragment and truncated forms of sclareol synthases may be used in the invention provided that these have the ability to catalyse the formation of (+)manool from (9S,10S)-copalyl diphosphate. It will further be understood that such, e.g. variant, fragment or truncated forms of sclareol synthease enzymes may have lost some or all of the ability to catalyse formation of sclareol from LPP without detracting from their suitability for use in the invention.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

An "isolated nucleic acid" or "isolated nucleic acid sequence" is defined as a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which it has not been intentionally modified by a human in the laboratory is naturally occurring.

"Recombinant nucleic acid sequence" are nucleic acid sequences that result from the use of laboratory methods (molecular cloning) to bring together genetic material from more than one source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3' non-translated sequence comprising, e.g., transcription termination sites.

A "chimeric gene" refers to any gene, which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3' end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein. "Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also include the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of a (+)-manool synthase in the organism.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a CPP synthase protein and a sclareol synthase protein or which together produce (+)-manool.

The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally.

Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

In one embodiment provided herein is a method for transforming a host cell or non-human organism with a nucleic acid encoding a polypeptide having a copalyl diphosphate synthase activity and with a nucleic acid encoding a polypeptide having a sclareol synthase activity wherein the polypeptide having the copalyl diphosphate activity comprises an amino acid sequence that has at least 90%, 95%, 98%, 99% or 100% sequence identity to a polypeptide selected from group consisting of SEQ ID NO: 1 and SEQ ID NO:2. Particularly, the polypeptide having the sclareol synthase activity comprises an amino acid sequence that has at least 90%, 95%, 98%, 99% or 100% sequence identity to a polypeptide selected from the group consisting SEQ ID NO:4 and SEQ ID NO:5.

In one embodiment provided herein is a method comprising cultivating a non-human host organism or cell capable of producing a geranylgeranyl diphosphate (GGPP) and transformed to express a polypeptide having a copalyl diphosphate synthase activity wherein the polypeptide having the copalyl diphosphate synthase activity comprises an amino acid sequence that has at least 90%, 95%, 98%, 99% or 100% sequence identity to a polypeptide selected from the group consisting of SEQ ID NO: 1 and SEQ ID NO:2 and further transformed to express a polypeptide having a sclareol synthase activity. Particularly, the polypeptide having the sclareol synthase activity comprises an amino acid sequence that has at least 90%, 95%, 98%, 99% or 100% sequence identity to a polypeptide selected from the group consisting SEQ ID NO:4 and SEQ ID NO:5.

Further provided herein is an expression vector comprising a nucleic acid encoding a CPP synthase wherein the CPP synthase comprises a polypeptide comprising an amino acid sequence that has at least 90%, 95%, 98%, 99% or 100% sequence identity to a polypeptide selected from the group consisting of SEQ ID NO: 1 and SEQ ID NO:2 and further the expression vector comprises a nucleic acid encoding a sclareol synthase enzyme. Particularly, the sclareol synthase has an amino acid sequence that is at least 90%, 95%, 98%, 99% or 100% similar or identical to a polypeptide selected from the group consisting SEQ ID NO:4 and SEQ ID NO:5. In a particularly embodiment, the two enzymes could be on two different vectors transformed in the same cell. In a further embodiment the two enzymes could be on two different vectors transformed in two different cells.

Further provided herein is a non-human host organism or cell transformed to harbor at least one nucleic acid encoding a CPP synthase wherein the CPP synthase comprises a polypeptide comprising an amino acid sequence that has at least 90%, 95%, 98%, 99% or 100% sequence identity to a polypeptide selected from the group consisting of SEQ ID NO: 1 and SEQ ID NO:2 and at least one nucleic acid encoding a sclareol enzyme. Particularly, the sclareol synthase has an amino acid sequence that is at least 90%, 95%, 98%, 99% or 100% similar or identical to a polypeptide selected from the group consisting SEQ ID NO:4 and SEQ ID NO:5.

In one embodiment, the nucleic acid that encodes for a CPP synthase provided herein comprises a nucleotide sequence that has at least 90%, 95%, 98%, 99% or 100% sequence identity to Sequence ID NO: 3.

In one embodiment, the nucleic acid that encodes for a CPP synthase provided herein comprises a nucleotide sequence that has at least 95%, 98%, 99% or 100% sequence identity to Sequence ID NO: 3.

In one embodiment, the nucleic acid that encodes for a CPP synthase provided herein comprises a nucleotide sequence that has at least 98%, 99% or 100% sequence identity to Sequence ID NO: 3.

In one embodiment, the nucleic acid that encodes for a CPP synthase provided herein comprises a nucleotide sequence that has at least 98%, 99% or 100% sequence identity to Sequence ID NO: 3.

In one embodiment, the nucleic acid that encodes for a CPP synthase provided herein comprises a nucleotide sequence that has 99% or 100% sequence identity to Sequence ID NO: 3. In one embodiment, the nucleic acid that encodes for a CPP synthase provided herein comprises a nucleotide sequence that is identical to Sequence ID NO: 3.

In one embodiment, the CPP synthase comprises a polypeptide comprising an amino acid sequence that has at least 90%, 95%, 98%, 99% or 100% sequence identity to a polypeptide selected from the group consisting of SEQ ID NO: 1 and SEQ ID NO:2

In one embodiment, the CPP synthase comprises a polypeptide comprising an amino acid sequence that has at least 90%, 95%, 98%, 99% or 100% sequence identity to SEQ ID NO: 1.

In one embodiment, the CPP synthase comprises a polypeptide comprising an amino acid sequence that has at least 95%, 98%, 99% or 100% sequence identity to a SEQ ID NO: 1

In one embodiment, the CPP synthase comprises a polypeptide comprising an amino acid sequence that has at least 98%, 99% or 100% sequence identity to SEQ ID NO: 1.

In one embodiment, the CPP synthase comprises a polypeptide comprising an amino acid sequence that has at least 99% or 100% sequence identity to SEQ ID NO: 1. In one embodiment, the CPP synthase comprises a polypeptide comprising an amino acid sequence that is identical to SEQ ID NO: 1.

In one embodiment, the CPP synthase comprises a polypeptide comprising an amino acid sequence that has at least 90%, 95%, 98%, 99% or 100% sequence identity to SEQ ID NO: 2.

In one embodiment, the CPP synthase comprises a polypeptide comprising an amino acid sequence that has at least 95%, 98%, 99% or 100% sequence identity to a SEQ ID NO: 2.

In one embodiment, the CPP synthase comprises a polypeptide comprising an amino acid sequence that has at least 98%, 99% or 100% sequence identity to SEQ ID NO: 2.

In one embodiment, the CPP synthase comprises a polypeptide comprising an amino acid sequence that has at least 99% or 100% sequence identity to SEQ ID NO: 2.

In one embodiment, the CPP synthase comprises a polypeptide comprising an amino acid sequence that is identical to SEQ ID NO: 2.

In one embodiment, the nucleic acid encoding the the sclareol synthase enzyme has a nucleotide sequence at least 90%, 95%, 98%, 99% or 100% similar or identical to SEQ ID NO.6.

In one embodiment the sclareol synthase has an amino acid sequence that is at least 90%, 95%, 98%, 99% or 100% similar or identical to SEQ ID NO: 4.

In one embodiment the sclareol synthase has an amino acid sequence that is at least 95%, 98%, 99% or 100% similar or identical to SEQ ID NO: 4.

In one embodiment the sclareol synthase has an amino acid sequence that is at least 98%, 99% or 100% similar or identical to SEQ ID NO: 4.

In one embodiment the sclareol synthase has an amino acid sequence that is at least 99% or 100% similar or identical to SEQ ID NO: 4.

In one embodiment the sclareol synthase has an amino acid sequence that is identical to SEQ ID NO: 4.

In one embodiment the sclareol synthase has an amino acid sequence that is at least 90%, 95%, 98%, 99% or 100% similar or identical to SEQ ID NO: 5.

In one embodiment the sclareol synthase has an amino acid sequence that is at least 95%, 98%, 99% or 100% similar or identical to SEQ ID NO: 5.

In one embodiment the sclareol synthase has an amino acid sequence that is at least 98%, 99% or 100% similar or identical to SEQ ID NO: 5.

In one embodiment the sclareol synthase has an amino acid sequence that is at least 99% or 100% similar or identical to SEQ ID NO: 5.

In one embodiment the sclareol synthase has an amino acid sequence that is identical to SEQ ID NO: 5.

In another embodiment, provided herein is an expression vector comprising a nucleic acid described herein. An expression vector may comprise one or more nucleic acids described herein.

In another embodiment, provided herein is a non-human host organism or cell transformed to harbor at least one nucleic acid described herein so that it heterologously expresses or over-expresses at least one polypeptide described herein.

In one embodiment, the non-human host organism provided herein is a plant, a prokaryote or a fungus.

In one embodiment, the non-human host provided herein is a microorganism, particularly a bacteria or yeast.

In one embodiment, the non-human organism provided herein is *E. coli* and said yeast is *Saccharomyces cerevisiae*.

In one embodiment, the non-human organism provided herein is *Saccharomyces cerevisiae*.

In one embodiment, the cell is a prokaryotic cell.

In other embodiment cell is a bacterial cell.

In one embodiment the cell is a eukaryotic cell.

In one embodiment the eukaryotic cell is a yeast cell or a plant cell.

In one embodiment, the process of producing (+)-manool produces the (+)-manool at a purity of at least 98% or 98.5%.

In another embodiment a method provided herein further comprises processing the (+)-manool to a derivative using a chemical or biochemical synthesis or a combination of both using methods commonly known in the art.

In one embodiment, the (+)-manool derivative is selected from the group consisting of an hydrocarbon, alcohol, acetal, aldehyde, acid, ether, ketone, lactone, acetate and an ester. According to any embodiment of the invention, said (+)-manool derivative is a $C_{10}$ to $C_{25}$ compound optionally comprising one, two or three oxygen atoms.

In a further embodiment, the derivative is selected from the group consisting of manool acetate ((3R)-3-methyl-5-[(1S,4aS,8aS)-5,5,8a-trimethyl-2-methylenedecahydro-1-naphthalenyl]-1-penten-3-yl acetate), copalol ((2E)-3-methyl-5-[(1S,4aS,8aS)-5,5,8a-trimethyl-2-methylenedecahydro-1-naphthalenyl]-2-penten-1-ol), copalol acetate ((2E)-3-methyl-5-[(1S,4aS,8aS)-5,5,8a-trimethyl-2-methylenedecahydro-1-naphthalenyl]-2-penten-1-yl acetate), copalal ((2E)-3-methyl-5-[(1S,4aS,8aS)-5,5,8a-trimethyl-2-methylenedecahydro-1-naphthalenyl]-2-pentenal), (+)-manooloxy (4-[(1S,4aS,8aS)-5,5,8a-trimethyl-2-methylenedecahydro-1-naphthalenyl]-2-butanone), Z-11 ((3S,5aR,7aS,11aS,11bR)-3,8,8,11a-tetramethyldodecahydro-3,5a-epoxynaphtho[2,1-c]oxepin), gamma-ambrol (2-[(1S,4aS,8aS)-5,5,8a-trimethyl-2-methylenedecahydro-1-naphthalenyl]ethanol) and Ambrox® (3aR,5aS,9aS,9bR)-3a, 6,6,9a-tetramethyldodecahydronaphtho[2,1-b]furan).

In another embodiment a method provided herein further comprises contacting the (+)-manool with a suitable reacting system to convert said (+)-manool in to a suitable (+)-manool derivative. Said suitable reacting system can be on enzymatic nature (e.g. requiring one or more enzymes) or of chemical nature (e.g. requiring one or more synthetic chemicals)

For example, (+)-manool may be enzymatically converted to manooloxy or gamma-ambrol using a processes described in the literature for example as set forth in U.S. Pat. No. 7,294,492, wherein said patent is incorporated by reference in its entirety herein.

In yet another embodiment, the (+)-manool derivative is copalol and its esters with a $C_1$-$C_5$ carboxylic acids.

In yet another embodiment, the (+)-manool derivative is a (+)-manool esters with a $C_1$-$C_5$ carboxylic acids.

In one embodiment, the (+)-manool derivative is copalal.

In one embodiment, the (+)-manool derivative is manooloxy.

In yet another embodiment, the (+)-manool derivative is Z-11.

In one embodiment, the (+)-manool derivative is gamma-ambrol or is a mixture thereof and its esters with a $C_1$-$C_5$ carboxylic acids, and in particular gamma-ambrol and its esters.

In a further embodiment, the (+)-manool derivative is Ambrox®, sclareolide (also known as 3a, 6,6,9a-tetramethyldecahydronaphtho[2,1-b]furan-2(1H)-one and all its diastereoisomer and stereoisomers), 3,4a, 7,7,10a-pentamethyldodecahydro-1H-benzo[f]chromen-3-ol or 3,4a, 7,7,10a-pentamethyl-4a, 5,6,6a, 7,8,9,10,10a, 10b-decahydro-1H-benzo[f]chromene and all their diastereoisomer and stereoisomers cyclic ketone and open form, (1R,2R,4aS, 8aS)-1-(2-hydroxyethyl)-2,5,5,8a-tetramethyldecahydronaphthalen-2-ol DOL, gamma-ambrol.

Specific examples of how said derivatives (e.g. a triene hydrocarbon, an acetate or copalol) can be obtained is detailed in the Examples.

For instance, the manool obtained according to the invention can be processed into Manooloxy (a ketone, as per known methods) and then into ambrol (an alcohol) and ambrox (an ether), according to EP 212254.

The ability of a polypeptide to catalyze the synthesis of a particular sesquiterpene can be confirmed by performing the enzyme assay as detailed in the Examples provided herein.

Polypeptides are also meant to include truncated polypeptides provided that they keep their (+)-manool synthase activity and their sclareol synthase activity. A truncated CPP synthase polypeptide for example has the activity of a CPP synthase as defined earlier herein. A truncated sclareol synthase polypeptide for example has the activity of a sclareol synthase as defined earlier herein.

As intended herein below, a nucleotide sequence obtained by modifying the sequences described herein may be performed using any method known in the art, for example by introducing any type of mutations such as deletion, insertion or substitution mutations. Examples of such methods are cited in the part of the description relative to the variant polypeptides and the methods to prepare them.

The percentage of identity between two peptide or nucleotide sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.*, 1999, 174:247-250, 1999) set to the default parameters, available from the National Center for Biotechnology Information (NCBI) at http://www.ncbi.nlm.nih.gov/BLAST/bl2seq/wblast2.cgi, can be used to obtain an optimal alignment of protein or nucleic acid sequences and to calculate the percentage of sequence identity.

The polypeptide to be contacted with GGPP in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

According to another particularly embodiment, the method of any of the above-described embodiments is carried out in vivo. These embodiments provided herein are particularly advantageous since it is possible to carry out the method in vivo without previously isolating the polypeptide. The reaction occurs directly within the organism or cell transformed to express said polypeptide.

Thus, for example, (+)manool may be produced from GGPP by cultivating a host cell or organism described herein.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. For example, a microorganism may be transformed with A particular organism or cell is meant to be "capable of producing GGPP" when it produces GGPP naturally or when it does not produce GGPP naturally but is transformed to produce GGPP, either prior to the transformation with a nucleic acid as described herein or together with said nucleic acid. Organisms or cells transformed to produce a higher amount of GGPP than the naturally occurring organism or cell are also encompassed by the "organisms or cells capable of producing GGPP". Methods to transform organisms, for example microorganisms, so that they produce GGPP are already known in the art.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. Most particularly, said bacteria is *E. coli* and said yeast is *Saccharomyces cerevisiae*.

Some of these organisms do not produce GGPP naturally or only in small amounts. To be suitable to carry out the method of an embodiment herein, these organisms have to be transformed to produce said precursor or to produce said precursor in larger amounts. They can be so transformed either before the modification with the nucleic acid described according to any of the above embodiments or simultaneously, as explained above.

An organism may be transformed, for example, with a nucleic acid encoding a GGPP synthase. The nucleic acid may be included in the same or different expression vector to a nucleic acid encoding a CPP synthase or a nucleic acid encoding a sclareol synthase as described herein. A GGPP synthase may, for example, comprise the amino acid sequence in SEQ ID NO: 7. A nucleic acid encoding a GGPP synthase may, for example, comprise the nucleic acid sequence in SEQ ID NO: 8. A transformation method such as that described herein and in the present Examples may be used.

An organism may be transformed with one or more nucleic acids encoding a part or a whole of the mevalonate pathway leading to FPP. A method such as that described in the present Examples may be used.

Isolated higher eukaryotic cells can also be used, instead of complete organisms, as hosts to carry out the method of an embodiment herein in vivo. Suitable eukaryotic cells may be any non-human cell, but are particularly plant or fungal cells.

According to another particular embodiment, the polypeptides having a CPP synthase activity and a sclareol synthase activity used in any of the embodiments described herein or encoded by the nucleic acids described herein may be variants obtained by genetic engineering, provided that said variant keeps its CPP synthase activity and its sclareol synthase activity. A variant CPP synthase polypeptide for example, has the activity of a CPP synthase as defined earlier herein. A variant sclareol synthase polypeptide for example has the activity of a sclareol synthase as defined earlier herein.

As used herein, the polypeptide is intended as a polypeptide or peptide fragment that encompasses the amino acid sequences identified herein, as well as truncated or variant polypeptides, provided that they keep their CPP synthase activity and their sclareol synthase activity as defined herein.

"Keeps activity" may, for example, mean that the polypeptide keeps at least some of the original activity of the unmutated, or non-truncated polypeptide, for example, at least 70, 80, 90. 95, 97, 99 or 100% of the activity. A variant or truncated polypeptide may, in some cases, have increased activity compared to the non-mutated or non-truncated polypeptide.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, encompassed herein are methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of an embodiment herein.

As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of an embodiment herein also encompass certain isolated nucleotide sequences including those that are substantially free from contaminating endogenous material. The nucleic acid of an embodiment herein may be truncated, provided that it encodes a polypeptide encompassed herein, as described above.

In one embodiment, the nucleic acid of an embodiment herein that encodes for a CPP synthase can be either present naturally in a plant such as *Salvia miltiorrhiza*, or other species, or be obtained by modifying SEQ ID NO: 3.

In a further embodiment, the nucleic acid of an embodiment herein that encodes for a sclareol synthase can be either present naturally in a plant such as *Salvia sclarea*, or other species, or can be obtained by modifying SEQ ID NO: 6.

Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the CPP synthase and the sclareol synthase may be optimized for increased expression in the host cell. For example, nucleotides of an embodiment herein may be synthesized using codons particular to a host for improved expression.

Another important tool for transforming host organisms or cells suitable to carry out the method of an embodiment herein in vivo is an expression vector comprising a nucleic acid according to any embodiment of an embodiment herein. Such a vector is therefore also provided herein. An expression vector may, for example, comprise one or more of a nucleic acid encoding a CPP synthase, a nucleic acid encoding a sclareol synthase or a nucleic acid encoding a GGPP synthase, as described herein.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and cells are therefore also provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods provided herein. Particularly useful plants are those that naturally produce high amounts of terpenes.

In a more particular embodiment the non-human host organism is a microorganism. Any microorganism is suitable to be used herein, but according to an even more particular embodiment said microorganism is a bacteria or yeast. Most particularly, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

A variant may also differ from the polypeptide of an embodiment herein by attachment of modifying groups which are covalently or non-covalently linked to the polypeptide backbone.

The variant also includes a polypeptide which differs from the polypeptide described herein by introduced N-linked or O-linked glycosylation sites, and/or an addition of cysteine residues. The skilled artisan will recognize how to modify an amino acid sequence and preserve biological activity.

Embodiments provided herein include, but are not limited to cDNA, genomic DNA and RNA sequences.

Genes, including the polynucleotides of an embodiment herein, can be cloned on basis of the available nucleotide sequence information, such as found in the attached sequence listing and by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

Provided herein are nucleic acid sequences obtained by mutations of SEQ ID NO: 3 and SEQ ID NO: 6; such mutations can be routinely made. It is clear to the skilled artisan that mutations, deletions, insertions, and/or substitutions of one or more nucleotides can be introduced into these DNA sequence The nucleic acid sequences of an embodiment herein encoding CPP synthase and the scalereol synthase proteins can be inserted in expression vectors and/or be contained in chimeric genes inserted in expression vectors, to produce CPP synthase and scaleol synthase in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

An embodiment provided herein provides recombinant expression vectors comprising a nucleic acid encoding for a CPP synthase and a scalereol synthase each, separately, are operably linked to associated nucleic acid sequences such as, for instance, promoter sequences.

Alternatively, the promoter sequence may already be present in a vector so that the nucleic acid sequence which is to be transcribed is inserted into the vector downstream of the promoter sequence. Vectors are typically engineered to have an origin of replication, a multiple cloning site, and a selectable marker.

EXAMPLES

Example 1

Diterpene Synthase Genes.

Two diterpene synthase are necessary for the conversion of geranylgeranyl-diphosphate (GGPP) to manool: a type II and a type I diterpene synthase. In these examples, for the the type II diterpene synthase, the copalyl-diphosphate (CPP) synthase *Salvia miltiorrhiza* (NCBI accession No ABV57835.1) was used. For optimal expression in *E. coli* cells the codon usage of the cDNA was optimized, the first 58 codons were removed and an ATG start codon was added. For the type I diterpene synthase, the sclareol synthase from *Salvia sclarea* (SsScS) was used (NCBI accession No AET21246.1, WO2009095366). The codon usage of the cDNA was optimized for *E. coli* expression (DNA 2.0, Menlo Park, Calif. 94025), the 50 first N-terminal codon were removed. Each of these two cDNAs was synthesized in-vitro and cloned in the pJ208 plasmid flanked with the NdeI and KpnI restriction enzyme recognition sites (DNA 2.0, Menlo Park, Calif. 94025, USA).

Example 2

Expression Plasmids.

The modified CPP synthase (SmCPS2) and sclareol synthase (SsScS) encoding cDNA was digested with NdeI and KpnI and ligated into the pETDuet-1 plasmid providing the pETDuet-SmCPS2 and pETDuet-1132opt expression plasmids, respectively.

Another plasmid was constructed to co-expression the SmCPS2 and SsScS enzymes together with a geranylgeranyl-diphophate (GGPP) synthase. For the GGPP synthase, the CrtE gene from *Pantoea agglomerans* (NCBI accession M38424.1) encoding for a GGPP synthase (NCBI accession number AAA24819.1) was used. The CrtE gene was synthesized with codon optimization and addition of the NcoI and BamHI restriction enzyme recognition sites at the 3' and 5' ends (DNA 2.0, Menlo Park, Calif. 94025, USA) and ligated between NcoI and BamHI site of the pETDuet-1 plasmid to obtain the pETDuet-CrtE plasmid. The modified SmCPS2 encoding cDNA was digested with NdeI and KpnI and ligated into the pETDuet-1-CrtE plasmid thus providing the pETDuet-CrtE-SmCPS2 construct. The optimized cDNA (Sa1132opt) encoding for the truncated SsScS was then introduced in the pETDuet-CrtE-SmCPS2 plasmid using the In-Fusion® technique (Clontech, Takara Bio Europe). For this cloning, the pETDuet-1132opt was used as template in a PCR amplification using the forward primer SmCPS2-1132Inf_F1 5'-CTGTTTGAGCCGGTCGC-CTAAGGTACCAGAAGGAGATAAATAATGGC-GAAAATGAAGGAGAACTTTAAACG-3' and the reverse primer 1132-pET_Inf_R1 5'-GCAGCGGTTTCTTTACCA-GACTCGAGGTCAGAACACGAAGCTCTTCATGTC-CTCT-3'. The PCR product was ligated in the plasmid pETDuet-CrtE-SmCPS2 digested with the KpnI and XhoI restriction enzymes and using the In-Fusion® Dry-Down PCR Cloning Kit (Clontech, Takara Bio Europe), providing the new plasmid pETDuet-CrtE-SmCPS2-SsScS. In this plasmid the CrtE gene is under the control of the first T7 promoter of the pETDuet plasmid and the CPP synthase and sclareol synthase encoding cDNAs are organized in a bi-cistronic construct under the control of the second T7 promoter.

Example 3

Heterologous Expression in *E. coli* and Enzymatic Activities.

The expression plasmids (pETDuet-SmCPS2 or pET-Duet-1132opt) were used to transformed B121(DE3) *E. Coli* cells (Novagene, Madison, Wis.). Single colonies of transformed cells were used to inoculate 25 ml LB medium. After 5 to 6 hours incubation at 37° C., the cultures were transferred to a 20° C. incubator and left 1 hour for equilibration. Expression of the protein was then induced by the addition of 0.1 mM IPTG and the culture was incubated over-night at 20° C. The next day, the cells were collected by centrifugation, re-suspended in 0.1 volume of 50 mM MOPSO pH 7, 10% glycerol, 1 mM DTT and lysed by sonication. The extracts were cleared by centrifugation (30 min at 20,000 g) and the supernatants containing the soluble proteins were used for further experiments.

Example 4

In-vitro Diterpene Synthase Activity Assays.

Enzymatic assays were performed in Teflon sealed glass tubes using 50 to 100 µl of protein extract in a final volume of 1 mL of 50 mM MOPSO pH 7, 10% glycerol supplemented with 20 mM $MgCl_2$ and 50 to 200 µM purified geranylgeranyl diphosphate (GGPP) (prepared as described by Keller and Thompson, J. Chromatogr 645(1), 161-167, 1993). The tubes were incubated 5 to 48 hours at 30° C. and the enzyme products were extracted twice with one volume of pentane. After concentration under a nitrogen flux, the extracts were analyzed by GC-MS and compared to extracts from control proteins (obtained from cells transformed with the empty plasmid). GC-MS analysis were performed on an Agilent 6890 series GC system equipped with a DB1 column (30 m×0.25 mm×0.25 mm film thickness; Agilent) and coupled with a 5975 series mass spectrometer. The carrier gas was helium at a constant flow of 1 ml/min. Injection was in split-less mode with the injector temperature set at 260° C. and the oven temperature was programmed from 100° C. to 225° C. at 10° C./min and to 280° C. at 30° C./min. The identities of the products were confirmed based on the concordance of the retention indices and mass spectra of authentic standards.

In these conditions and with the recombinant protein from *E. coli* cells transformed with the plasmids pETDuet-SmCPS2 or pETDuet-1132opt (heterologously expressing the SmCPS or SsScS enzymes, respectively) no production of diterpene molecules was detected in the solvent extracts (the diphosphate-containing diterpenes are not detected in these conditions). Similar assays were then performed but combining the 2 protein extracts containing the recombinant SmCPS and SsScS in a single assay. In these assays, one major product was formed and was identified as being (+)-manool by matching of the mass spectrum and retention index with authentic standards (FIG. 2).

Example 5

In-vivo Manool production using *E. coli* cells.

The in-vivo production of manool using cultures of whole cells was evaluated using *E. coli* cells. To increase the level of endogenous farnesyl-diphosphate (FPP) pool the productivity in diterpene of the cells, an heterologous complete mevalonate pathway leading to FPP was co-expressed in the same cells. The enzymes of this pathway were expressed using a single plasmid containing all the genes organized in two operons under the control of two promoters. The construction of this expression plasmid is described in patent WO2013064411 or in Schalk et al (2013) J. Am. Chem. Soc. 134, 18900-18903. Briefly, a first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

KRX *E. coli* cells (Promega) were co-transformed with the plasmid pACYC-29258-4506 and the pETDuet-CrtE-SmCPS2-SsScS plasmid. Transformed cells were selected on carbenicillin (50 µg/ml) and chloramphenicol (34 µg/ml) LB-agarose plates. Single colonies were used to inoculate 5 mL liquid LB medium supplemented with the same antibiotics. The culture were incubated overnight at 37° C. The next day 2 mL of TB medium supplemented with the same antibiotics were inoculated with 0.2 mL of the overnight culture. After 6 hours incubation at 37° C., the culture was cooled down to 28° C. and 0.1 mM IPTG, 0.2% rhamnose and 1:10 volume of decane were added to each tube. The cultures were incubated for 48 hours at 28° C. The cultures were then extracted twice with 2 volumes of MTBE (Methyl tert-butyl ether), the organic phase were concentrated to 500 µL and analyzed by GC-MS as described above in example 4 except for the oven temperature which was 1 min hold at 100° C., followed by a temperature gradient of 10° C./min to 220° C. and 20° C./min and to 3000° C. In this culture conditions manool was produced as the only diterpene product and with an yield of 300 to 500 mg/L (FIG. 3).

Example 6

Production of (+)-manool Using Recombinant Cells, Purification and NMR Analysis.

One litter of *E. coli* culture was prepared in the conditions described in example 5 except that the decane organic phase was replace by 50 g/L Amberlite XAD-4 for solide phase extaction. The culture medium was filtered to recover the resine. The resine was then washed with 3 column volumes of water, and eluted using 3 column volumes of MTBE. The product was then further purified by flash chromatography on silica gel using a mobile phase composed of heptane:MTBE 8:2 (v/v). The structure of manool was confirmed by 1H- and 13C-NMR. The optical rotation was measured using a Bruker Avance 500 MHz spectrometer. The value of $[\alpha]^D_{20}=+26.9°$ (0.3%, $CHCl_3$) confirmed the production of (+)-manool.

Example 7

The manool obtained in the above examples was converted into its esters according to the following experimental part (herein below as example into its acetate):

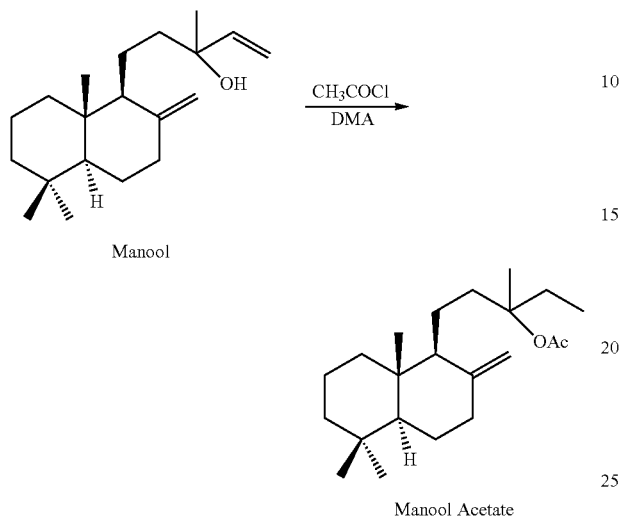

Following the literature (G. Ohloff, *Helv. Chim. Acta* 41, 845 (1958)), 32.0 g (0.11 mole) of pure crystalline (+)-Manool were treated by 20.0 g (0.25 mole) of acetyl chloride in 100 ml of dimethyl aniline for 5 days at room temperature. The mixture was additionally heated for 7 hours at 50° to reach 100% of conversion. After cooling, the reaction mixture was diluted with ether, washed successively with 10% $H_2SO_4$, aqueous $NaHCO_3$ and water to neutrality. After drying ($Na_2SO_4$) and concentration, the product was distilled (bulb-to-bulb, B.p.=160°, 0.1 mbar) to give 20.01 g (79.4%) of Manool Acetate which was used without further purification.

MS: $M^+332$ (0); m/e: 272 (27), 257 (83), 137 (62), 95 (90), 81 (100).

$^1$H-NMR ($CDCl_3$): 0.67, 0.80, 0.87, 1.54 and 2.01 (5 s, 3H each), 4.49 (s, 1H), 4.80 (s, 1H), 5.11 (m, 1H), 5.13 (m, 1H), 5.95 (m, 1H).

$^{13}$C-NMR ($CDCl_3$): 14.5 (q), 17.4 (t), 19.4 (t), 21.7 (q), 22.2 (q), 23.5 (q), 24.2 (t), 33.5 (s), 33.6 (t), 38.3 (t), 39.0 (t), 39.3 (t), 39.8 (s), 42.2 (t), 55.6 (d), 57.2 (t), 83.4 (s), 106.4 (t), 113.0 (t), 142.0 (d), 148.6 (s), 169.9 (s).

Example 8

The manool acetate obtained in the above examples was converted into its trienes according to the following experimental part (herein below as example into its Sclarene and (Z+E)-Biformene):

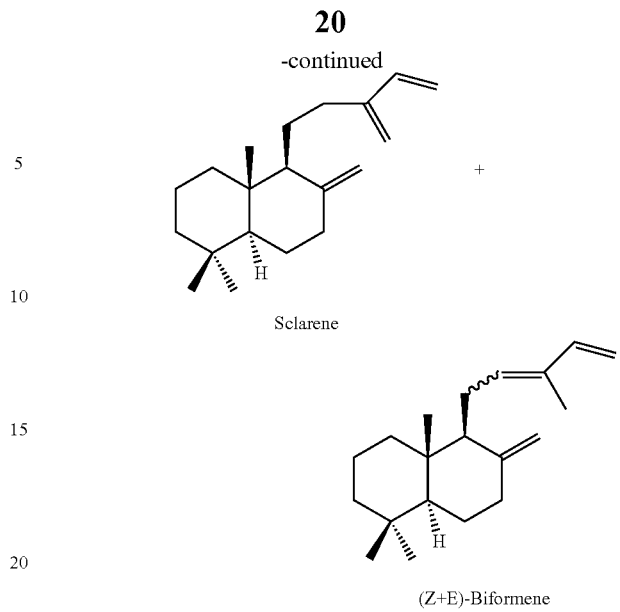

To a solution of 0.4 g of Manool Acetate in 4 ml of cyclohexane at room temperature was added 0.029 g (0.05 eq.) of $BF_3$.AcOH complex. After 15 minutes at room temperature, the reaction was quenched with aqueous $NaHCO_3$ and washed with water to neutrality. GC-MS analysis showed only hydrocarbons which were identified as Sclarene, (Z) and (E)-biformene. No Copalol Acetate was detected.

Another trial with more catalyst (0.15 eq) gave the same result.

Sclarene: MS: $M^+272$ (18); m/e: 257 (100), 149 (15), 105 (15).

(Z) and (E)-Biformene (identical spectra): MS: $M^+272$ (29); m/e: 257 (100), 187 (27), 161 (33), 105 (37).

Example 9

The manool obtained in the above examples was converted into Copalyl esters according to the following experimental part (herein below as example into the acetate):

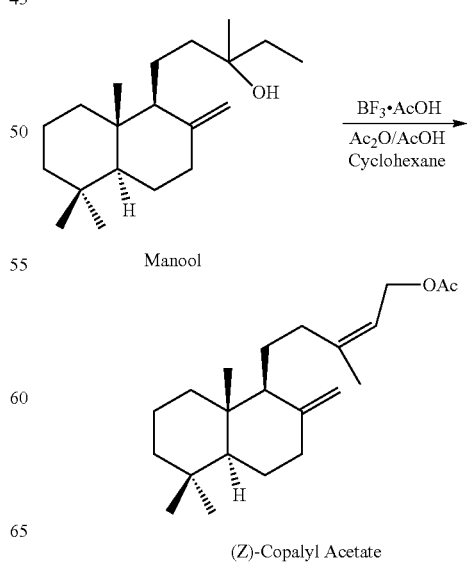

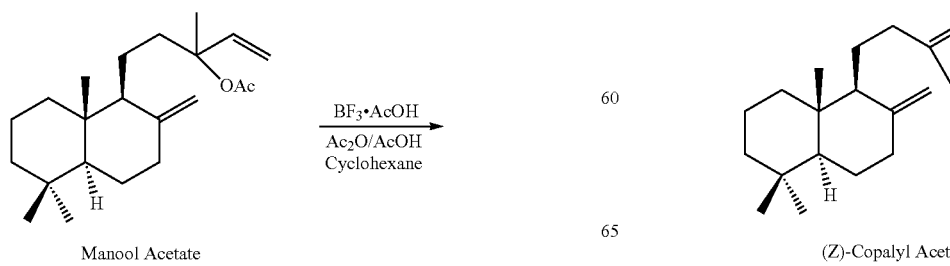

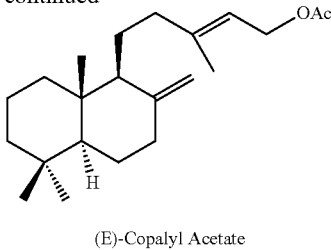

(E)-Copalyl Acetate

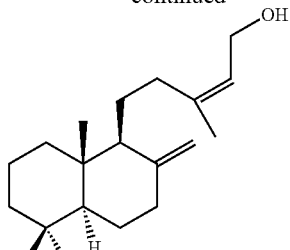

(Z)-Copalol

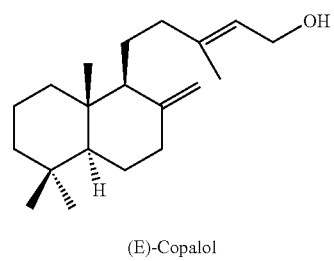

(E)-Copalol

To a solution of 0.474 g (0.826 mmole, 0.27 eq.) of $BF_3$.AcOH in 100 ml of cyclohexane at room temperature was added 4.4 g of acetic anhydride and 12.1 g of acetic acid. At room temperature, 10.0 g (33 mmole) of pure crystalline Manool in 15 ml of cyclohexane were added (sl. exothermic) and the temperature was maintained at room temperature using a water bath. After 30 min. of stirring at room temperature, a GC control showed no starting material. The reaction mixture was quenched with 300 ml of aq. saturated $NaHCO_3$ and treated as usual. The crude mixture (9.9 g) was purified by flash chromatography (SiO2, pentane/ether 95:5) and bulb-to-bulb distillation (Eb.=130°, 0.1 mbar) to give 4.34 g (37.1%) of a 27/73 mixture of (Z) and (E)-Copalyl Acetate.

(Z)-Copalyl Acetate

MS: $M^+$332 (0); m/e: 317 (2), 272 (35)=, 257 (100), 137 (48), 95 (68), 81 (70).

$^1$H-NMR ($CDCl_3$): 0.67, 0.80, 0.87 1.76 and 2.04 (5 s, 3H each), 4.86 (s, 1H), 5.35 (t: J=6 Hz, 1H).

(E)-Copalyl Acetate

MS: $M^+$332 (0); m/e: 317 (2), 272 (33)=, 257 (100), 137 (54), 95 (67), 81 (74).

$^1$H-NMR ($CDCl_3$): 0.68, 0.80, 0.87 1.70 and 2.06 (5 s, 3H each), 4.82 (s, 1H), 5.31 (t: J=6 Hz, 1H).

$^{13}$C-NMR ($CDCl_3$): (Spectrum recorded on (Z/E) mixture, only significant signals are given): 61.4 (t), 106.2 (t), 117.9 (d), 143.1 (s), 148.6 (s), 171.1 (s).

Example 10

The copalyl acetate obtained in the above examples was converted into Copalol according to the following experimental part:

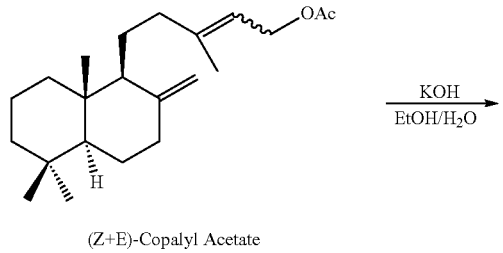

(Z+E)-Copalyl Acetate $\xrightarrow{\text{KOH}}{\text{EtOH/H}_2\text{O}}$

Copalyl Acetate (4.17 g, 12.5 mmole), KOH pellets (3.35 g, 59.7 mmole), water (1.5 g) and EtOH (9.5 ml) were mixed together and stirred for 3 hours at 50°. After usual workup, 3.7 g of crude (Z+E)-Copalol were obtained and purified by flash chromatography (SiO2, pentane/ether 7:2. After evaporation of the solvent, a bulb-to-bulb distillation (Eb=170°, 0.1 mbar) furnished 3.25 g (92%) of a 27/73 mixture of (Z) and (E)-Copalol.

(Z)-Copalol

MS: $M^+$290 (3); m/e: 275 (18), 272 (27), 257 (82), 137 (71), 95 (93), 81 (100), 69 (70).

$^1$H-NMR ($CDCl_3$): 0.67, 0.80, 0.87 and 1.74 (4 s, 3H each); 4.06 (m, 2H), 4.55 (s, 1H), 4.86 (s, 1H), 5.42 (t: J=6 Hz, 1H).

(E)-Copalol

MS: $M^+$290 (3); m/e: 275 (27), 272 (22), 257 (75), 137 (75), 95 (91), 81 (100), 69 (68).

$^1$H-NMR ($CDCl_3$): 0.68, 0.80, 0.87 and 1.67 (4 s, 3H each); 4.15 (m, 2H), 4.51 (s, 1H), 4.83 (s, 1H), 5.39 (t, J=6 Hz, 1H)

$^{13}$C-NMR ($CDCl_3$): (Spectrum recorded on (Z/E) mixture, only significant signals are given): 59.4 (t), 106.2 (t), 123.0 (d), 140.6 (s), 148.6 (s).

NMR analysis are in good agreement with published spectra for similar compounds. For example, see S. Hasecawa, Y. Hirose, *Phytochemistry* 19 (11), 2479 (1980).

```
Sequence listing.

SmCPS, full-length copalyl-diphosphate synthase from S. miltiorrhiza
                                                         SEQ ID NO: 1
MASLSSTILSRSPAARRRITPASAKLHRPECFATSAWMGSSSKNLSLSYQLNHKKISVAT
VDAPQVHDHDGTTVHQGHDAVKNIEDPIEYIRTLLRTTGDGRISVSPYDTAWVAMIKDV
EGRDGPQFPSSLEWIVQNQLEDGSWGDQKLFCVYDRLVNTIACVVALRSWNVHAHKV
KRGVTYIKENVDKLMEGNEEHMTCGFEVVFPALLQKAKSLGIEDLPYDSPAVQEVYHV
REQKLKRIPLEIMHKIPTSLLFSLEGLENLDWDKLLKLQSADGSFLTSPSSTAFAFMQTKD
EKCYQFIKNTIDTFNGGAPHTYPVDVFGRLWAIDRLQRLGISRFFEPEIADCLSH
IHKFWTDKGVFSGRESEFCDIDDTSMGMRLMRMHGYDVDPNVLRNFKQKDGKFSCYG
```

```
GQMIESPSPIYNLYRASQLRFPGEEILEDAKRFAYDFLKEKLANNQILDKWVISKHLPDEI
KLGLEMPWLATLPRVEAKYYIQYYAGSGDVWIGKTLYRMPEISNDTYHDLAKTDFKRC
QAKHQFEWLYMQEWYESCGIEEFGISRKDLLLSYFLATASIFELERTNERIAWAKSQIIA
KMITSFFNKETTSEEDKRALLNELGNINGLNDTNGAGREGGAGSIALATLTQFLEGFDRY
TRHQLKNAWSVWLTQLQHGEADDAELLTNTLNICAGHIAFREEILAHNEYKALSNLTSK
ICRQLSFIQSEKEMGVEGEIAAKSSIKNELEEDMQMLVKLVLEKYGGIDRNIKKAFLAV
AKTYYYRAYHAADTIDTHMFKVLFEPVA

SmCPS2, truncated copalyl diphosphate synthase from S. miltiorrhiza
                                                                    SEQ ID NO: 2
MATVDAPQVHDHDGTTVHQGHDAVKNIEDPIEYIRTLLRTTGDGRISVSPYDTAWVAMI
KDVEGRDGPQFPSSLEWIVQNQLEDGSWGDQKLFCVYDRLVNTIACVVALRSWNVHA
HKVKRGVTYIKENVDKLMEGNEEHMTCGFEVVFPALLQKAKSLGIEDLPYDSPAVQEV
YHVREQKLKRIPLEIMHKIPTSLLFSLEGLENLDWDKLLLKLQSADGSFLTSPSSTAFAFM
QTKDEKCYQFIKNTIDTFNGGAPHTYPVDVFGRLWAIDRLQRLGISRFFEPEIADCLSHIH
KFWTDKGVFSGRESEFCDIDDTSMGMRLMRMHGYDVDPNVLRNFKQKDGKFSCYGG
QMIESPSPIYNLYRASQLRFPGEEILEDAKRFAYDFLKEKLANNQILDKWVISKHLPDEIK
LGLEMPWLATLPRVEAKYYIQYYAGSGDVWIGKTLYRMPEISNDTYHDLAKTDFKRCQ
AKHQFEWLYMQEWYESCGIEEFGISRKDLLLSYFLATASIFELERTNERIAWAKSQIIAK
MITSFFNKETTSEEDKRALLNELGNINGLNDTNGAGREGGAGSIALATLTQFLEGFDRYT
RHQLKNAWSVWLTQLQHGEADDAELLTNTLNICAGHIAFREEILAHNEYKALSNLTSKI
CRQLSFIQSEKEMGVEGEIAAKSSIKNELEEDMQMLVKLVLEKYGGIDRNIKKAFLAV
AKTYYYRAYHAADTIDTHMFKVLFEPVA SmCPS2opt, optimized cDNA encoding for SmCPS2
                                                                    SEQ ID NO: 3
ATGGCAACTGTTGACGCACCTCAAGTCCATGATCACGATGGCACCACCGTTCACCAG
GGTCACGACGCGGTGAAGAACATCGAGGACCCGATCGAATACATTCGTACCCTGCT
GCGTACCACTGGTGATGGTCGCATCAGCGTCAGCCCGTATGACACGGCGTGGGTGG
CGATGATTAAAGACGTCGAGGGTCGCGATGGCCCGCAATTTCCTTCTAGCCTGGAGT
GGATTGTCCAAAATCAGCTGGAAGATGGCTCGTGGGGTGACCAGAAGCTGTTTTGTG
TTTACGATCGCCTGGTTAATACCATCGCATGTGTGGTTGCGCTGCGTAGCTGGAATG
TTCACGCTCATAAAGTCAAACGTGGCGTGACGTATATCAAGGAAAACGTGGATAAG
CTGATGGAAGGCAACGAAGAACACATGACGTGTGGCTTCGAGGTTGTTTTTCCAGCC
TTGCTGCAGAAAGCAAAGTCCCTGGGTATTGAGGATCTGCCGTACGACTCGCCGGCA
GTGCAAGAAGTCTATCACGTCCGCGAGCAGAAGCTGAAACGCATCCCGCTGGAGAT
TATGCATAAGATTCCGACCTCTCTGCTGTTCTCTCTGGAAGGTCTGGAGAACCTGGA
TTGGGACAAACTGCTGAAGCTGCAGTCCGCTGACGGTAGCTTTCTGACCAGCCCGAG
CAGCACGGCCTTTGCGTTTATGCAGACCAAAGATGAGAAGTGCTATCAATTCATCAA
GAATACTATTGATACCTTCAACGGTGGCGCACCGCACACGTACCCAGTAGACGTTTT
TGGTCGCCTGTGGGCGATTGACCGTTTGCAGCGTCTGGGTATCAGCCGTTTCTTCGA
GCCGGAGATTGCGGACTGCTTGAGCCATATTCACAAATTCTGGACGGACAAAGGCG
TGTTCAGCGGTCGTGAGAGCGAGTTCTGCGACATCGACGATACGAGCATGGGTATG
CGTCTGATGCGTATGCACGGTTACGACGTGGACCCGAATGTGTTGCGCAACTTCAAG
CAAAAAGATGGCAAGTTTAGCTGCTACGGTGGCCAAATGATTGAGAGCCCGAGCCC
GATCTATAACTTATATCGTGCGAGCCAACTGCGTTTCCCGGGTGAAGAAATTCTGGA
AGATGCGAAGCGTTTTGCGTATGACTTCCTGAAGGAAAAGCTCGCAAACAATCAAA
TCTTGGATAAATGGGTGATCAGCAAGCACTTGCCGGATGAGATTAAACTGGGTCTGG
AGATGCCGTGGTTGGCCACCCTGCCGAGAGTTGAGGCGAAATACTATATTCAGTATT
ACGCGGGTAGCGGTGATGTTTGGATTGGCAAGACCCTGTACCGCATGCCGGAGATC
AGCAATGATACCTATCATGACCTGGCCAAGACCGACTTCAAACGCTGTCAAGCGAA
ACATCAATTTGAATGGTTATACATGCAAGAGTGGTACGAAAGCTGCGGCATCGAAG
AGTTCGGTATCTCCCGTAAAGATCTGCTGCTGTCTTACTTTCTGGCAACGGCCAGCAT
TTTCGAGCTGGAGCGTACCAATGAGCGTATTGCCTGGGCGAAATCACAAATCATTGC
TAAGATGATTACGAGCTTTTTCAATAAAGAAACCACGTCCGAGGAAGATAAACGTG
CTCTGCTGAATGAACTGGGCAACATCAACGGTCTGAATGACACCAACGGTGCCGGT
CGTGAGGGTGGCGCAGGCAGCATTGCACTGGCCACGCTGACCCAGTTCCTGGAAGG
TTTCGACCGCTACACCCGTCACCAGCTGAAGAACGCGTGGTCCGTCTGGCTGACCCA
GCTGCAGCATGGTGAGGCAGACGACGCGGAGCTGCTGACCAACACGTTGAATATCT
GCGCTGGCCATATCGCGTTTCGCGAAGAGATTCTGGCGCACAACGAGTACAAAGCC
CTGAGCAATCTGACCTCTAAAATCTGTCGTCAGCTTAGCTTTATTCAGAGCGAGAAA
GAAATGGGCGTGGAAGGTGAGATCGCGGCAAAATCCAGCATCAAGAACAAAGAAC
TGGAAGAAGATATGCAGATGTTGGTCAAGCTCGTCCTGGAGAAGTATGGTGGCATC
GACCGTAATATCAAGAAAGCGTTTCTGGCCGTGGCGAAAACGTATTACTACCGCGC
GTACCACGCGGCAGATACCATTGACACCCACATGTTTAAGGTTTTGTTTGAGCCGGT
TGCTTAA Full-length sclareol synthase
                                                                    SEQ ID NO: 4
MSLAFNVGVTPFSGQRVGSRKEKFPVQGFPVTTPNRSRLIVNCSLTTIDFMAKMKENFK
REDDKFPTTTTLRSEDIPSNLCIIDTLQRLGVDQFFQYEINTILDNTFRLWQEKHKVIYGN
VTTHAMAFRLLRVKGYEVSSEELAPYGNQEAVSQQTNDLPMIIELYRAANERIYEEERS
LEKIIAWTTIFLNKQVQDNSIPDKKLHKLVEFYLRNYKGITIRLGARRNLELYDMTYYQ
ALKSTNRFSNLCNEDFLVFAKQDFDIHEAQNQKGLQQLRWYADCRLDTLNFGRDVVII
ANYLASLIIGDHAFDYVRLAFAKTSVLVTIMDDFFDCHGSSQECDKIIELVKEWKENPDA
EYGSEELEILFMALYNTVNELAERARVEQGRSVKEFLVKLWVEILSAFKIELDTWSNGT
QQSFDEYISSSWLSNGSRLTGLLTMQFVGVKLSDEMLMSEECTDLARHVCMVGRLLND
```

-continued

Sequence listing.

VCSSEREREENIAGKSYSILLATEKDGRKVSEDEAIAEINEMVEYHWRKVLQIVYKKESI
LPRRCKDVFLEMAKGTFYAYGINDELTSPQQSKEDMKSFVF truncated sclareol synthase (SsScS).
SEQ ID NO: 5

MAKMKENFKREDDKFPTTTTLRSEDIPSNLCIIDTLQRLGVDQFFQYEINTILDNTFRLWQ
EKHKVIYGNVTTHAMAFRLLRVKGYEVSSEELAPYGNQEAVSQQTNDLPMIIELYRAA
NERIYEEERSLEKILAWTTIFLNKQVQDNSIPDKKLHKLVEFYLRNYKGITIRLGARRNLE
LYDMTYYQALKSTNRFSNLCNEDFLVFAKQDFDIHEAQNQKGLQQLQRWYADCRLDT
LNFGRDVVIIANYLASLIIGDHAFDYVRLAFAKTSVLVTIMDDFFDCHGSSQECDKIIELV
KEWKENPDAEYGSEELEILFMALYNTVNELAERARVEQGRSVKEFLVKLWVEILSAFKI
ELDTWSNGTQQSFDEYISSSWLSNGSRLTGLLTMQFVGVKLSDEMLMSEECTDLARHV
CMVGRLLNDVCSSEREREENIAGKSYSILLATEKDGRKVSEDEAIAEINEMVEYHWRKV
LQIVYKKESILPRRCKDVFLEMAKGTFYAYGINDELTSPQQSKEDMKSFVF 1132-2-5_opt, optimized cDNA encoding for the truncated sclareol synthase.
SEQ ID NO: 6

ATGGCGAAAATGAAGGAGAACTTTAAACGCGAGGACGATAAATTCCCGACGACCAC
GACCCTGCGCAGCGAGGATATCCCGAGCAACCTGTGCATCATTGATACCCTGCAGC
GCCTGGGTGTCGATCAGTTCTTCCAATACGAAATCAATACCATTCTGGACAATACTT
TTCGTCTGTGGCAAGAGAAACACAAAGTGATCTACGGCAACGTTACCACCCACGCG
ATGGCGTTCCGTTTGTTGCGTGTCAAGGGCTACGAGGTTTCCAGCGAGGAACTGGCG
CCGTACGGTAATCAGGAAGCAGTTAGCCAACAGACGAATGATCTGCCTATGATCATT
GAGCTGTATCGCGCAGCAAATGAGCGTATCTACGAAGAGGAACGCAGCCTGGAAAA
GATCCTGGCGTGGACCACGATCTTCCTGAACAAACAAGTTCAAGACAATTCTATTCC
TGATAAGAAGCTGCATAAACTGGTCGAATTCTATCTGCGTAATTACAAGGGCATCAC
GATCCGTCTGGGCGCACGCCGTAACCTGGAGTTGTATGATATGACGTATTACCAGGC
TCTGAAAAGCACCAATCGTTTCTCCAATCTGTGTAATGAGGATTTTCTGGTGTTCGCC
AAGCAGGATTTTGACATCCACGAGGCGCAAAATCAAAAAGGTCTGCAACAACTGCA
ACGTTGGTACGCTGACTGTCGCCTGGACACCCTGAATTTCGGTCGCGACGTTGTCAT
TATTGCAAACTATCTGGCCAGCCTGATCATCGGTGATCACGCATTCGACTACGTCCG
CCTGGCCTTCGCTAAGACCAGCGTTCTGGTGACCATTATGGATGATTTCTTCGATTGC
CACGGTTCTAGCCAGGAATGCGACAAAATCATTGAGCTGGTGAAAGAGTGGAAAGA
AAACCCTGATGCGAATACGGTTCCGAAGAGTTGGAGATCCTGTTTATGGCCTTGTA
CAACACCGTGAATGAACTGGCCGAGCGTGCTCGTGTGGAGCAGGGCCGTTCTGTGA
AGGAGTTTTTGGTCAAGTTGTGGGTGGAAATCCTGTCCGCGTTCAAGATCGAACTGG
ATACGTGGTCGAATGGTACGCAACAGAGCTTCGACGAATACATCAGCAGCAGCTGG
CTGAGCAATGGCAGCCGTCTGACCGGTTTGCTGACCATGCAATTTGTGGGTGTTAAA
CTGTCCGATGAAATGCTGATGAGCGAAGAATGCACCGACCTGGCACGCCATGTGTG
TATGGTGGGTCGCCTGCTGAACGACGTCTGCAGCAGCGAACGTGAGCGCGAGGAAA
ACATTGCAGGCAAGAGCTACAGCATCTTGTTGGCCACCGAGAAAGATGGTCGCAAA
GTGTCTGAGGACGAAGCAATTGCAGAGATTAATGAAATGGTCGAGTACCACTGGCG
TAAGGTTTTGCAGATTGTGTATAAGAAAGAGAGCATCTTGCCGGTCTGCGTGTAAGGA
TGTTTTCTTGGAGATGGCGAAGGGCACGTTCTATGCGTACGGCATTAACGACGAGCT
GACGAGCCCGCAACAATCGAAAGAGGACATGAAGAGCTTCGTGTTCTGAGGTAC

GGPP synthase from Pantoea agglomerans.
SEQ ID NO: 7
MVSGSKAGVSPHREIEVMRQSIDDHLAGLLPETDSQDIVSLAMREGVMAPGKRIRPLLM
LLAARDLRYQGSMPTLLDLACAVELTHTASLMLDDMPCMDNAELRRGQPTTHKKFGE
SVAILASVGLLSKAFGLIAATGDLPGERRAQAVNELSTAVGVQGLVLGQFRDLNDAALD
RTPDAILSTNHLKTGILFSAMLQIVAIASASSPSTRETLHAFALDFGQAFQLLDDLRDDHP
ETGKDRNKDAGKSTLVNRLGADAARQKLREHIDSADKHLTFACPQGGAIRQFMHLWF
GHHLADWSPVMKIA CrtEopt, optimized cDNA encoding for the GGPP synthase from Pantoea agglomerans.
SEQ ID NO: 8
ATGGTTTCTGGTTCGAAAGCAGGAGTATCACCTCATAGGGAAATCGAAGTCATGAG
ACAGTCCATTGATGACCACTTAGCAGGATTGTTGCCAGAAACAGATTCCCAGGATAT
CGTTAGCCTTGCTATGAGAGAAGGTGTTATGGCACCTGGTAAACGTATCAGACCTTT
GCTGATGTTACTTGCTGCAAGAGACCTGAGATATCAGGGTTCTATGCCTACACTACT
GGATCTAGCTTGTGCTGTTGAACTGACACATACTGCTTCCTTGATGCTGGATGACAT
GCCTTGTATGGACAATGCGGAACTTAGAAGAGGTCAACCAACAACCCACAAGAAAT
TCGGAGAATCTGTTGCATTTTGGCTTCTGTAGGTCTGTTGTCGAAAGCTTTTGGCTT
GATTGCTGCAACTGGTGATCTTCCAGGTGAAAGGAGAGCACAAGCTGTAAACGAGC
TATCTACTGCAGTTGGTGTTCAAGGTCTAGTCTTAGGACAGTTCAGAGATTTGAATG
ACGCAGCTTTGGACAGAACTCCTGATGCTATCCTGTCTACGAACCATCTGAAGACTG
GCATCTTGTTCTCAGCTATGTTGCAAATCGTAGCCATTGCTTCTGCTTCTTCACCATC
TACTAGGGAAACGTTACACGCATTCGCATTGGACTTTGGTCAAGCCTTTCAACTGCT
AGACGATTTGAGGGATGATCATCCAGAGACAGGTAAAGACCGTAACAAAGACGCTG
GTAAAAGCACTCTAGTCAACAGATTGGGTGCTGATGCAGCTAGACAGAAACTGAGA
GAGCACATTGACTCTGCTGACAAACACCTGACATTTGCATGTCCACAAGGAGGTGCT
ATAAGGCAGTTTATGCACCTATGGTTTGGACACCATCTTGCTGATTGGTCTCCAGTG
ATGAAGATCGCCTAA

The invention claimed is:

1. A method of producing (+)-manool comprising:
   a. contacting geranylgeranyl diphosphate with an copalyl diphosphate (CPP) synthase to form a (9S, 10S)-copalyl diphosphate wherein the CPP synthase comprises an amino acid sequence having at least 90%, 95%, 98%, 99% and 100% sequence identity to SEQ ID NO: 1 or SEQ ID NO:2; and
   b. contacting the (9S, 10S)-copalyl diphosphate CPP with a sclareol synthase enzyme to form (+)-manool; and
   c. optionally isolating the (+)-manool.

2. The method as recited in claim 1, wherein the sclareol synthase comprises an amino acid sequence that has at least 90%, 95%, 98%, 99% and 100% sequence identity to SEQ ID NO:4 or SEQ ID NO:5.

3. The method as recited in claim 1, further comprising processing the (+)-manool to a (+)-manool derivative using a chemical or biochemical synthesis or a combination of both.

4. The method as recited in claim 3, wherein the derivative is an alcohol, acetal, aldehyde, acid, ethers, ketone, lactone, acetate or ester.

5. The method as recited in claim 4, wherein the derivative is selected from the group consisting of capalol, capalal, (+)-manooloxy, Z-11, gamma-ambrol and ambrox.

* * * * *